(12) United States Patent
Fisher

(10) Patent No.: US 7,449,565 B2
(45) Date of Patent: Nov. 11, 2008

(54) CHIMERIC TUMOR SUPPRESSOR GENE AND PROTEIN

(75) Inventor: Paul B Fisher, Scarsdale, NY (US)

(73) Assignee: The Trustees of Columbia University in the City of New York, New York, NY (US)

( * ) Notice: Subject to any disclaimer, the term of this patent is extended or adjusted under 35 U.S.C. 154(b) by 268 days.

(21) Appl. No.: 11/040,219

(22) Filed: Jan. 21, 2005

(65) Prior Publication Data

US 2006/0166220 A1    Jul. 27, 2006

(51) Int. Cl.
| | |
|---|---|
| C07H 21/04 | (2006.01) |
| C07H 21/02 | (2006.01) |
| A01N 43/04 | (2006.01) |
| A01N 63/00 | (2006.01) |
| A01N 65/00 | (2006.01) |
| A61K 31/70 | (2006.01) |
| A61K 48/00 | (2006.01) |
| C12N 15/00 | (2006.01) |

(52) U.S. Cl. .................. 536/23.4; 536/23.1; 536/24.2; 514/44; 424/93.1; 424/93.21; 435/320.1

(58) Field of Classification Search ................ None
See application file for complete search history.

(56) References Cited

U.S. PATENT DOCUMENTS

| 6,146,877 A | 11/2000 | Fisher |
| 6,472,520 B2 | 10/2002 | Fisher |
| 6,737,523 B1 | 5/2004 | Fisher et al. |

FOREIGN PATENT DOCUMENTS

| WO | WO 98/42315 | 10/1998 |
| WO | WO 99/49898 | 10/1999 |
| WO | WO 02/08242 | 7/2001 |

OTHER PUBLICATIONS

Su, et al. (1999) Proc. Natl. Acad. Sci., USA., 96(26): 15115-20.*
Hollander, et al. (2003) Oncogene, 22: 3827-32.*
Emdad et al. 2005 Progression elevated gene-3 (PEG-3) induces pleiotropic effects on tumor progression: modulation of genomic stability and invasion. J Cell Physiol. 202(1):135-46.
Su et al, Online Publication Jan. 17, 2005, Potential molecular mechanism for rodent tumorigenesis: mutational generation of Progression Elevated Gene-3 (PEG-3) Oncogene 24(13):2247-55.
Shi et al., 2004, GADD34-PP1c recruited by Smad7 dephosphorylates TGF-β type I receptor. J. Cell Biol. 164: 291-300.
Brush et al., 2003, Growth Arrest and DNA Damage-Inducible Protein GADD34 Targets Protein Phosphatase 1α to the Endoplasmic Reticulum and Promotes Dephosphorylation of the α Subunit of Eukaryotic Translation Initiation Factor 2. Mol. Cell. Biol. 23: 1292-303.
Hollander et al., 2003, Gadd34 functional domains involved in growth suppression and apoptosis. Oncogene 22: 3827-3832.

Kojima et al., 2003, The function of GADD34 is a recovery from a shutoff of protein synthesis induced by ER stress: elucidation by GADD34-deficient mice. Faseb J. 17: 1573-1575.
Yagi et al., 2003, GADD34 induces p53 phosphorylation and p21/WAF1 transcription. J. Cell Biochem. 90: 1242-1249.
Greco et al. 2002, Cancer gene therapy: 'delivery, delivery, delivery'. Front Biosci. 7:1516-24.
Sarkar et al., 2002, mda-7 (IL-24) Mediates selective apoptosis in human melanoma cells by inducing the coordinated overexpression of the GADD family of genes by means of p38 MAPK. Proc. Natl. Acad. Sci. U.S.A. 99: 10054-10059.
Su et al., 2002, Progression elevated gene-3, PEG-3, induces genomic instability in rodent and human tumor cells. J Cell Physiol 192(1): 34-44.
Connor et al., 2001, Growth Arrest DNA Damage-Inducible Protein GADD34 Assembles a Novel Signaling Complex Containing Protein Phosphatase 1 and Inhibitor 1. Mol. Cell Biol. 21: 6841-50.
Grishin et al., 2001, Interaction between growth arrest-DNA damage protein 34 and Src kinase Lyn negatively regulates genotoxic apoptosis. Proc. Natl. Acad. Sci. U.S.A. 98: 10172-10177.
Hollander et al., 2001, Activation of Gadd34 by diverse apoptotic signals and suppression of its growth inhibitory effects by apoptotic inhibitors. Int. J. Cancer 96: 22-31.
Novoa et al., 2001, Feedback inhibition of the unfolded protein response by GADD34-mediated dephosphorylation of eIF2alpha. J. Cell Biol. 153: 1011-22.
Su, Z. et al., 2001, PEA3 sites within the progression elevated gene-3 (PEG-3) promoter and mitogen-activated protein kinase contribute to differential PEG-3 expression in Ha-ras and v-raf oncogene transformed rat embryo cells. Nucleic Acids Res 29, 1661-1671.
DOE Joint Genome Institute (2000) GenBank Accession No. AC073828 215734 bp DNA Mus musculus clone RP23-9J18, Working Draft Sequence, 21 unordered pieces. Direct Submission (Jun. 29, 2000).
Fox (2000) "Malaria Public Health Burden Expands, Inspires Novel Strategies". ASM News (American Society for Microbiology), 66 (2): 1-3.
Hasegawa et al., 2000, Interaction between DNA-damage protein GADD34 and a new member of the Hsp40 family of heat shock proteins that is induced by a DNA-damaging reagent. Biochem. J. 352 Pt 3: 795-800.
Hasegawa et al., 2000, Interaction between GADD34 and kinesin superfamily, KIF3A. Biochem. Biophys. Res. Commun. 267: 593-6.
Luo et al., 2000, Synthetic DNA delivery systems, ture Biotechnol. 18:33-37.
Su, Z. et al., 2000, Cooperation between AP1 and PEA3 sites within the progression elevated gene-3 (PEG-3) promoter regulate basal and differential expression of PEG-3 during progression of the oncogenic phenotype in transformed rat embryo cells. Oncogene 19: 3411-3421.

(Continued)

*Primary Examiner*—Robert M. Kelly
(74) *Attorney, Agent, or Firm*—Baker Botts LLP

(57) ABSTRACT

The present invention relates to chimeric molecules comprising portions of rat PEG-3 ("rPEG-3") and human GADD34 ("hGADD34") having apoptotic activity. It is based, at least in part, on the discovery that a chimeric protein comprising amino acids 1-347 of rat PEG-3 fused with residues 418-674 of human GADD34 exhibited anti-proliferative activity when expressed in transformed cells. The present invention provides for this and other rPEG3/hGADD34 chimeras, and the use of such proteins in inhibiting cell proliferation, angiogenesis, and tumor growth.

7 Claims, 17 Drawing Sheets

OTHER PUBLICATIONS

Figure 1:
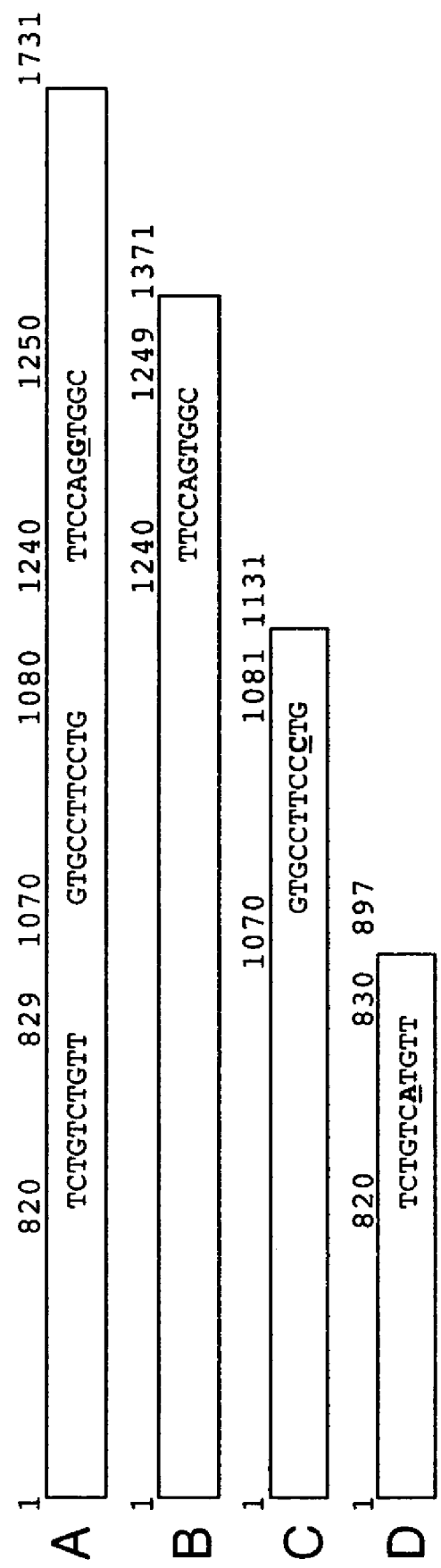

Adler et al., 1999, Leukemic HRX fusion proteins inhibit GADD34-induced apoptosis and associate with the GADD34 and hSNF5/INI1 proteins. Mol. Cell Biol. 19: 7050-60.

Bulavin et al., 1999, Phosphorylation of human p53 by p38 kinase coordinates N-terminal phosphorylation and apoptosis in response to UV radiation. EMBO J. 18: 6845-6854.

Fisher et al., Geneseq. Accession No. AAV65766. Feb. 2, 1999, Accessed Apr. 6, 2002.

Hasegawa and Isobe, 1999, Evidence for the interaction between Translin and GADD34 in mammalian cells. Biochim Biophys Acta 1428: 161-8.

Palu t al., 1999, In pursuit of new developments for gene therapy of human diseases, J. Biotechnol. 68:1-13.

Su, Z. Z. et al., 1999, PEG-3, a nontransforming cancer progression gene, is a positive regulator of cancer aggressiveness and angiogenesis. Proc Natl Acad Sci U S A 96: 15115-15120.

Anderson 1998, Human gene therapy. Nature 392(6679 Suppl):25-30.

Boado et al., 1998 Drug delivery of antisense molecules to the brain for treatment of Alzheimer's disease and cerebral AIDS. J Pharm Sci. 87(11):1308-15.

Kang D., et al., (1998) "Cloning of progression elevated and Proc. progression suppressed genes by reciprocal subtraction RNA display" Am Assoc Can Res., 39:347 Abstract #2368.

Takekawa et al., 1998, A family of stress-inducible GADD45-like proteins mediate activation of the stress-responsive MTK1/MEKK4 MAPKKK. Cell 95: 521-530.

Hollander, M.C. and Fornace, A.J. Jr., GenBank Sequence Accession No. U83984, Direct Submission by Jan. 7, 1997, Mus musculus apoptosis associated protein (GADD34) gene, promoter sequence, accessed Apr. 6, 2002.

Hollander, M.C. and Fornace, A.J. Jr., 1997, GenBank Sequence Accession No. HSU83981, Direct Submission Jan. 7, 1997. *Homo sapiens* apoptosis associated protein (GADD34) mRNA.

Fisher and Su, 1997 GenBank Accession Nos. AF020618, complete cds submitted Aug. 25, 1997, Rattus norvegicus progression elevated gene 3 protein mRNA.

Hollander et al., 1997, Mammalian GADD34, an apoptosis- and DNA damage-inducible gene. J. Biol. Chem. 272(21): 13731-13737.

Su, Z. Z. et al., 1997, Subtraction hybridization identifies a transformation progression-associated gene PEG-3 with sequence homology to a growth arrest and DNA damage-inducible gene. Proc Natl Acad Sci U S A 94: 9125-9130.

Verma et al., 1997, Gene therapy—promises, problems and prospects, Nature 389:239-242.

He, B. et al., 1996, The carboxyl terminus of the murine MyD116 gene substitutes for the corresponding domain of the gamma (1)34.5 gene of herpes simplex virus to preclude the premature shutoff of total protein synthesis in infected human cells. J Virol 70: 84-90.

Ross et al. (1996) Gene therapy in the United States: a five-year status report. Human Gene Therapy, 7:1781-1790.

Su, Z.-Z., et al. (1996) "Surface-epitope Masking and Expression Cloning Identifies the Human Prostate Carcinoma Tumor Antigen Gene PCTA-1 a Member of the Galectin Gene Family," Proc Natl Acad Sci USA 93:7252-7257.

Vairapandi et al. (1996) The differentiation primary response gene MyD118, related to GADD45, encodes for a nuclear protein which interacts with PCNA and p21.sup. WAF1/cip1, Oncogene 11:2579-2594.

Crystal, Ronald G. (1995) Transfer of genes to humans: early lessons and obstacles to success, Science 270:404-410.

Orkin and Motulsky, co-chairs Report and recommendations of the panel to assess the NIH investment in research on gene therapy, National Institute of Health, Dec. 7, 1995.

Shen, R., et al. (1995) Identification of the human prostatic carcinoma oncogene PTI-1 by rapid expression cloning and differential RNA display. Proc. Natl. Acad. of Sci., USA 92:6778-6782.

Stull, et al. (1995) Antigene, ribozyme and aptamer nucleic acid drugs: Progress and prospects, Pharm. Res., 12:465-483.

Chou, J. and Roizman, B., 1994, Herpes simplex virus 1 gamma(1)34.5 gene function, which blocks the host response to infection, maps in the homologous domain of the genes expressed during growth arrest and DNA damage. Proc Natl Acad Sci U S A 91: 5247-5251.

Jiang et al. (1994) A molecular definition of terminal cell differentiation in human melanoma cells. Mol. Cell Different, 2:(3):221-239.

Zhan, Q. et al., 1994, The gadd and MyD genes define a novel set of mammalian genes encoding acidic proteins that synergistically suppress cell growth. Mol Cell Biol 14: 2361-2371.

Jiang, H. and P. Fisher (1993) "Use of a Sensitive and Efficient Subtraction Hybridization Protocol for the Identification of Genes Differentially Regulated During the Induction of Differentiation in Human Melanoma Cells." Mol Cell Different. 1:285-299.

Reddy, P. G., et al. (1993) "Identification and Cloning of Genes.sub.—Involved in Progression of Transformed Phenotype," in Chromosome and Genetic Analysis, Methods in Molecular Genetics, ed. Adolph, K. W. (Academic, Orlando FL), vol. 1, pp. 68-102.

Su, Z. Z. et al., 1993, Defining the critical gene expression changes associated with expression and suppression of the tumorigenic and metastatic phenotype in Ha-ras-transformed cloned rat embryo fibroblast cells. Oncogene 8: 1211-1219.

Su et al. (1991) "Suppression of Adenovirus Type 5 E1A-Mediated Transformation and Expression of the Transformed Phenotype by Caffeic Acid Phenethyl Ester (CAPE)," Mol. Carcinog 4:231-242.

Su et al. (1991) "Induction of Transformation Progression in Type 5 Adenovirus-transformed Ray Embryo Cells by a Cloned Protein Kinase C .beta..sub.1 Gene and Reversal of Progression by 5-azacytidine," Oncogene 9:1123-1132.

* cited by examiner

FIGURE 12

```
MAPSP RPQHV LHWKE AHSFY LLSPL MGFLS RAWSR LRGPE VSEAW LAETV
AGANQ IEADA LLTPP PVSEN HLPLR ETEGN GTPEW SKAAQ RLCLD VEAQS
SPPKT WGLSD IDEHN GKPGQ DGLRE QEVEH TAGLP TLQPL HLQGA DKKVG
EVVAR EEGVS ELAYP TSHWE GGPAE DEEDT ETVKK AHQAS AASIA PGYKP
STSVY CPGEA EHRAT EEKGT DNKAE PSGSH SRVWE YHTRE RPKQE GETKP
EQHRA GQSHP CQNAE AEEGG PETSV CSGSA FLKAW VYRPG EDTEE EEDSD
LDSAE EDTAH TCTTP HTSAF LKAWV YRPGE DTEEE DDGDW DSAEE DASQS
CTTPH TSAFL KAWVY RPGED TEEED DSENV APVDS ETVDS CQSTQ HCLPV
EKTKG CGEAE PPPFQ WPSIY LDRSQ HHLGL PLSCP FDCRS GSDLS KPPPG
IRALR FL
```

FIGURE 13

```
MAPGQ APHQA TPWRD AHPFF LLSPV MGLLS RAWSR LRGLG PLEPW LVEAV
KGAAL VEAGL EGEAR TPLAI PHTPW GRRPE EEAED SGGPG EDRET LGLKT
SSSLP EAWGL LDDDD GMYGE REATS VPRGQ GSQFA DGQRA PLSPS LLIRT
LQGSD KNPGE EKAEE EGVAE EEGVN KFSYP PSHRE CCPAV EEEDD EEAVK
KEAHR TSTSA LSPGS KPSTW VSCPG EEENQ ATEDK RTERS KGARK TSVSP
RSSGS DPRSW EYRSG EASEE KEEKA HKETG KGEAA PGPQS SAPAQ RPQLK
SWWCQ PSDEE EGEVK ALGAA EKDGE AECPP CIPPP SAFLK AWVYW PGEDT
EEEED EEEDE DSDSG SDEEE GEAEA SSSTP ATGVF LKSWV YQPGE DTEEE
EDEDS DTGSA EDERE AETSA STPPA SAFLK AWVYR PGEDT EEEED EDVDS
EDKED DSEAA LGEAE SDPHP SHPDQ RAHFR GWGYR PGKET EEEEA AEDWG
EAEPC PFRVA IYVPG EKPPP PWAPP RLPLR LQRRL KRPET PTHDP DPETP
LKARK VRFSE KVTVH FLAVW AGPAQ AARQG PWEQL ARDRS RFARR ITQAQ
EELSP CLTPA ARARA WARLR NPPLA PIPAL TQTLP SSSVP SSPVQ TTPLS
QAVAT PSRSS AAAAA ALDLS GRRG
```

FIGURE 14

```
ctgcagtact tgtacattgc taaataaaga gagggactcc aggaggagca gcctgggtct   60
aagaggtagg cagaaggagg ttttaggggc ctgagcacaa gcttgaggag agaaaggtta  120
ttaaaaagcc agacgcttac aggtctcaga agggctagcc agaaactgtg gctgggtta   180
aggaaagggt ttaagagtgt gggcttttgg ttctgaggat gtagaacgtg aatgttgaga  240
gaagaaccaa gtggcggagt tgggtgtgag caatgctatt aggaatttga ggcagggatt  300
cacgcgctgc tgtgactatt ttttaacaat gactcagtgc tgtgacctga tactgtttcc  360
agagcgactt ctaaacaaat tccccctttc taggccagac acatggcccc aagcccaaga  420
ccccagcatg tcctgcactg gaaggaagcc cactctttct acctcctgtc tccactgatg  480
ggcttcctca gccgggcctg gagccgcctg aggggcccg aggtctcaga ggcctggttg    540
gcagaaacag tagcaggagc aaaccagata gaggctgatg ctctgttgac gcctccccg   600
gtctctgaaa atcacctacc tctccgagag actgaaggaa atgaactcc tgaatggagt   660
aaagcagccc agaggctctg ccttgatgtg gaagcccaaa gttcccctcc taaaacttgg  720
ggactttcag atattgatga acataatggg aagccaggac aagatggcct tagagagcaa  780
gaagtggagc acacagctgg cctgcctaca ctacagcccc ttcacctgca agggcagat   840
aagaaagttg gggaggtggt ggctagagaa gagggtgtgt ccgagctggc ttaccccaca  900
tcacactggg agggtggtcc agctgaggat gaagaggata cagaaaccgt gaagaaggct  960
caccaggcct ctgctgcttc catagctcca ggatataaac ccagcacttc tgtgtattgc 1020
ccaggggagg cagaacatcg agccacggag gaaaaaggaa cagacaataa ggctgaaccc 1080
tcaggctccc actccagagt ctgggagtac cacactagag agaggcctaa gcaggaggga 1140
gaaactaagc cagagcaaca cagggcaggg cagtcacc cttgtcagaa tgcagaggct   1200
gaggaaggag gacctgagac ttctgtctgt tctggcagtg ccttcctgaa ggcctgggtg 1260
tatcgcccag gagaggacac agaggaggaa gaagacagtg atttggattc agctgaggaa 1320
gacacagctc atacctgtac caccccccat acaagtgcct tcctgaaggc ctgggtctat 1380
cgcccaggag aggacacaga agaggaagat gacggtgatt gggattcagc tgaggaagac 1440
gcgtctcaga gctgtaccac ccccatca agtgccttcc tgaaggcctg ggtctatcgc   1500
ccaggagagg acacagaaga ggaagacgac agtgagaatg tggccccagt tgactcagaa 1560
acagttgact cttgccagag tacccagcat tgtctaccag tagagaagac caagggatgt 1620
ggagaagcag agccccctcc cttccagtgg ccttctattt acctggacag aagccagcac 1680
caccttgggc tgcccctaag ctgccccttc gactgcagaa gcggctcaga tctttcaaag 1740
cccccgcccg gaatcagggc cctgagattc ctctgaaggg tagaaaggtg cacttctctg 1800
agaaagttac agtccatttc cttgctgtct gggcaggacc agcccaggct gctcgtcgag 1860
gcccctggga gcagtttgca cgagatcgaa gccgctttgc tcgacgcatt gccaggcaga 1920
ggagcagctg ggtccttacc ttaccctgc tttcagggcc agagcatgga cacgccttag  1980
aaacctaccc cttcctctgt cgtcctcgtc tcttccactg cctgagcctt gctcttccac 2040
tgaggccaca cccctcagcc aagatgtgac cactccctct ccccttccca gtgaaatccc 2100
tcctcccagc ctggacttgg gaggaaggcg ggctaagcct gagtagtttt ttgtgtattc 2160
tatgagtgtt agtctcttaa tacgaatatg taacgccttt tgcatttgta aaaaaaaaa  2220
aaaaa //
```

FIGURE 15

```
cccagttgtt gatcttatgc aagacgctgc acgacccgc gcccgcttgt cgccacggca 60
cttgaggcag ccggagatac tctgagttac tcggagcccg acgcctgagg gtgagatgaa 120
cgcgctggcc tccctaaccg tccggacctg tgatcgcttc tggcagaccg aaccggcgct 180
cctgccccg gggtgacgcg cagctcccag ccgcccagac acatggcccc aggccaagca 240
ccccatcagg ctacccgtg gagggatgcc cacccttct tcctcctgtc cccagtgatg 300
ggcctcctca gccgcgcctg gagccgcctg aggggcctgg gacctctaga gccctggctg 360
gtggaagcag taaaaggagc agctctggta gaagctggcc tggagggaga agctaggact 420
cctctggcaa tcccccatac cccttggggc agacgccctg aagaggaggc tgaagacagt 480
ggaggccctg gagaggacag agaaacactg gggctgaaaa ccagcagttc ccttcctgaa 540
gcctggggac ttttggatga tgatgatggc atgtatggtg agcgagaggc aaccagtgtc 600
cctagagggc agggaagtca atttgcagat ggccagcgtg ctcccctgtc tccagccttt 660
ctgataagga cactgcaagg ttctgataag aacccagggg aggagaaagc cgaggaagag 720
ggagttgctg aagaggaggg agttaacaag ttctcttatc caccatcaca ccgggagtgt 780
tgtccagccg tggaggagga ggacgatgaa gaagctgtaa agaaagaagc tcacagaacc 840
tctacttctg ccttgtctcc aggatccaag cccagcactt gggtgtcttg cccaggggag 900
gaagagaatc aagccacgga ggataaaaga acagaaagaa gtaaggagc caggaagacc 960
tccgtgtccc cccgatcttc aggctccgac cccaggtcct gggagtatcg ttcaggagag 1020
gcgtccgagg agaaggagga aaaggcacac aaagaaactg ggaaaggaga agctgcccca 1080
gggccgcaat cctcagcccc agcccagagg ccccagctca agtcctggtg gtgccaaccc 1140
agtgatgaag aggagggtga ggtcaaggct ttgggggcag ctgagaagga tggagaagct 1200
gagtgtcctc cctgcatccc ccaccaagt gccttcctga aggcctgggt gtattggcca 1260
ggagaggaca cagaggaaga ggaagatgag gaagaagatg aggacagtga ctctggatca 1320
gatgaggaag agggagaagc tgaggcttcc tcttccactc ctgctacagg tgtcttcttg 1380
aagtcctggg tctatcagcc aggagaggac acagaggagg aggaagatga ggacagtgat 1440
acaggatcag ccgaggatga aagagaagct gagacttctg cttccacacc ccctgcaagt 1500
gctttcttga aggcctgggt gtatcggcca ggagaggaca cggaggagga ggaagatgag 1560
gatgtggata gtgaggataa ggaagatgat tcagaagcag ccttgggaga agctgagtca 1620
gacccacatc cctcccaccc ggaccagagg gcccacttca ggggctgggg atatcgacct 1680
ggaaaagaga cagaggaaga ggaagctgct gaggactggg gagaagctga gccctgcccc 1740
ttccgagtgg ccatctatgt acctggagag aagccaccgc ctccctgggc tcctcctagg 1800
ctgccctcc gactgcaaag gcggctcaag cgcccagaaa ccctactca tgatccggac 1860
cctgagactc ccctaaaggc cagaaaggtg cgcttctccg agaaggtcac tgtccatttc 1920
ctggctgtct gggcagggcc ggcccaggcc gcccgccagg gccctggga gcagcttgct 1980
cgggatcgca gccgcttcgc acgccgcatc acccaggccc aggaggagct gagccctgc 2040
ctcaccctg ctgccgggc cagagcctgg gcacgcctca ggaacccacc tttagcccc 2100
atccctgccc tcacccagac cttgccttcc tcctctgtcc cttcgtcccc agtccagacc 2160
acgcccttga gccaagctgt ggccacacct tcccgctcgt ctgctgctgc agcggctgcc 2220
ctggacctca gtgggaggcg tggctgagac caactggttt gcctataatt tattaactat 2280
ttatttttc taagtgtggg tttatataag gaataaagcc ttttgatttg t
```

FIGURE 16

MAPSPRPQHVLHWKEAHSFYLLSPLMGFLSRAWSRLRGPEVSEAWLAETVAGANQIEADALLTPPPVSENHLPLRET
EGNGTPEWSKAAQRLCLDVEAQSSPPKTWGLSDIDEHNGKPGQDGLREQEVEHTAGLPTLQPLHLQGADKKVGEVVA
REEGVSELAYPTSHWEGGPAEDEEDTETVKKAHQASAASIAPGYKPSTSVYCPGEAEHRATEEKGTDNKAEPSGSHS
RVWEYHTRERPKQEGETKPEQHRAGQSHPCQNAEAEEGGPETSVCSGSAFLKAWVYRPGEDTEEEEDSDLDSAEEDT
AHTCTTPHTSAFLKAWVYRPGEDTEEEDDGDWDSAEEDALTSASTPPASAFLKAWVYRPGEDTEEEEDEDVDSEDKE
DDSEAALGEAESDPHPSHPDQRAHFRGWGYRPGKETEEEEAAEDWGEAEPCPFRVAIYVPGEKPPPPWAPPRLPLRL
QRRLKRPETPTHDPDPETPLKARKVRFSEKVTVHFLAVWAGPAQAARQGPWEQLARDRSRFARRITQAQEELSPCLT
PAARARAWARLRNPPLAPIPALTQTLPSSSVPSSPVQTTPLSQAVATPSRSSAAAAAALDLSGRRG

FIGURE 17

```
ATGGCCCCAAGCCCAAGACCCCAGCATGTCCTGCACTGGAAGGAAGCCCACTCTTTCTACCTCCTGTCTCCACTGAT
GGGCTTCCTCAGCCGGGCCTGGAGCCGCCTGAGGGGGCCCGAGGTCTCAGAGGCCTGGTTGGCAGAAACAGTAGCAG
GAGCAAACCAGATAGAGGCTGATGCTCTGTTGACGCCTCCCCCGGTCTCTGAAAATCACCTACCTCTCCGAGAGACT
GAAGGAAATGGAACTCCTGAATGGAGTAAAGCAGCCCAGAGGCTCTGCCTTGATGTGGAAGCCCAAAGTTCCCCTCC
TAAAACTTGGGGACTTTCAGATATTGATGAACATAATGGGAAGCCAGGACAAGATGGCCTTAGAGAGCAAGAAGTGG
AGCACACAGCTGGCCTGCCTACACTACAGCCCCTTCACCTGCAAGGGGCAGATAAGAAAGTTGGGGAGGTGGTGGCT
AGAGAAGAGGGTGTGTCCGAGCTGGCTTACCCCACATCACACTGGGAGGGTGGTCCAGCTGAGGATGAAGAGGATAC
AGAAACCGTGAAGAAGGCTCACCAGGCCTCTGCTGCTTCCATAGCTCCAGGATATAAACCCAGCACTTCTGTGTATT
GCCCAGGGGAGGCAGAACATCGAGCCACGGAGGAAAAGGAACAGACAATAAGGCTGAACCCTCAGGCTCCCACTCC
AGAGTCTGGGAGTACCACACTAGAGAGAGGCCTAAGCAGGAGGGAGAAACTAAGCCAGAGCAACACAGGGCAGGGCA
GAGTCACCCTTGTCAGAATGCAGAGGCTGAGGAAGGAGGACCTGAGACTTCTGTCTGTTCTGGCAGTGCCTTCCTGA
AGGCCTGGGTGTATCGCCCAGGAGAGGACACAGAGGAGGAAGAAGACAGTGATTTGGATTCAGCTGAGGAAGACACA
GCTCATACCTGTACCACCCCCATACAAGTGCCTTCCTGAAGGCCTGGGTCTATCGCCCAGGAGAGGACACAGAAGA
GGAAGATGACGGTGATTGGGATTCAGCTGAGGAAGACGCGTTGACTTCTGCTTCCACACCCCTGCAAGTGCTTTCT
TGAAGGCCTGGGTGTATCGGCCAGGAGAGGACACGGAGGAGGAGGAAGATGAGGATGTGGATAGTGAGGATAAGGAA
GATGATTCAGAAGCAGCCTTGGGAGAAGCTGAGTCAGACCCACATCCCTCCCACCCGGACCAGAGGGCCCACTTCAG
GGGCTGGGGATATCGACCTGGAAAAGAGACAGAGGAAGAGGAAGCTGCTGAGGACTGGGGAGAAGCTGAGCCCTGCC
CCTTCCGAGTGGCCATCTATGTACCTGGAGAGAAGCCACCGCCTCCCTGGGCTCCTCCTAGGCTGCCCCTCCGACTG
CAAAGGCGGCTCAAGCGCCCAGAAACCCCTACTCATGATCCGGACCCTGAGACTCCCCTAAAGGCCAGAAAGGTGCG
CTTCTCCGAGAAGGTCACTGTCCATTTCCTGGCTGTCTGGGCAGGGCCGGCCCAGGCCGCCCGCCAGGGCCCCTGGG
AGCAGCTTGCTCGGGATCGCAGCCGCTTCGCACGCCGCATCACCCAGGCCCAGGAGGAGCTGAGCCCCTGCCTCACC
CCTGCTGCCCGGCCAGAGCCTGGGCACGCCTCAGGAACCCACCTTTAGCCCCCATCCCTGCCCTCACCCAGACCTT
GCCTTCCTCCTCTGTCCCTTCGTCCCCAGTCCAGACCACGCCCTTGAGCCAAGCTGTGGCCACACCTTCCCGCTCGT
CTGCTGCTGCAGCGGCTGCCCTGGACCTCAGTGGGAGGCGTGGCTGA
```

CHIMERIC TUMOR SUPPRESSOR GENE AND PROTEIN

GRANT INFORMATION

The subject matter of this application was developed in part under National Institutes of Health grant CA35675, so that the United States Government has certain rights herein.

1. INTRODUCTION

The present invention relates to a novel tumor suppressor gene and protein. It is based, at least in part, on the discovery that a chimeric molecule comprising portions of the rat PEG-3 gene and the human GADD34 gene encoded a protein having anti-cancer activity.

2. BACKGROUND OF THE INVENTION

Progression elevated gene-3 (PEG-3) was cloned from a tumor progression model based on rat embryo cells (Babiss et al., 1985, Science 228: 1099-1101; Fisher et al., 1978, Proc Natl Acad Sci USA 75: 2311-2314; Su et al., 1997, Proc Natl Acad Sci USA 94: 9125-9130). E11 is a mutant adenovirus type 5 (H5ts125)-transformed rat embryo cell clone that forms small, slow-growing and compact tumors. E11-NMT is a clone of E11 that has been selected for aggressiveness by passage through a nude mouse and forms rapidly growing, highly aggressive tumors (Babiss et al., 1985, Science 228: 1099-1101). Subtraction hybridization of an E11 cDNA library from an E11-NMT cDNA library identified PEG-3 (Su et al., 1997, Proc Natl Acad Sci USA 94: 9125-9130). Elevated PEG-3 expression has been documented in E11-NMT cells in comparison with E11 cells and also in normal cloned rat embryo fibroblast (CREF) cells displaying a transformed/tumorigenic phenotype, as a consequence of expression of diverse acting oncogenes, including Ha-ras, v-src, human papilloma virus type-18-transforming genes and a specific mutant of Ad5 (H5hr1), relative to parental CREF cells (Su et al., 1997, Proc Natl Acad Sci USA 94: 9125-9130). Ectopic expression of PEG-3 in E11 cells markedly augments in vitro anchorage independent growth and increases their oncogenic potential in nude mice as reflected by a shorter tumor latency time and the production of larger tumors with increased vascularization (Su et al., 1997, Proc Natl Acad Sci USA 94: 9125-9130; Su et al., 1999, Proc Natl Acad Sci USA 96: 15115-15120). As a corollary, E11-NMT cells stably expressing antisense PEG-3 lose their progressed cancer phenotype (Su et al., 1999, Proc Natl Acad Sci USA 96: 15115-15120). Overexpression of PEG-3 induces genomic instability, modulates the expression of important genes involved in centrosomal duplication and augments the invasive capability by increasing matrix metalloproteinase activity indicating that PEG-3 facilitates tumor progression by multiple pathways (Su et al., 2002, J Cell Physiol 192: 34-44).

When it was cloned, PEG-3 was observed to have high homology to hamster GADD34, except that it lacked the unique carboxy-terminal domain of GADD34 that is conserved in all species (Su et al., 1997, Proc. Natl. Acad. Sci. U.S.A. 94:125-130). GADD34 is a member of the Growth Arrest and DNA Damage ("GADD") inducible family of genes (Fornace et al., 1989, Mol. Cell Bio. 9:4196-4203; Takekawa et al., 1998, Cell 95:521-530; Zhan et al., 1994, Mol. Cell Biol. 14:2361-2371). GADD34 was first identified in hamsters (Fornace et al., 1989, Mol. Cell Bio. 9:4196-4203), and subsequently has been identified in human (Hollander et al., 1997, J. Biol. Chem. 272:13731-13737), mouse (as Myd116; Lord et al., 1990. Nucl. Acids Res. 18:2823) and rat; it exhibits high homology and similar domain structure across species. Induction of GADD34 has been shown to be associated with induction of apoptosis by diverse mechanisms and overexpression of GADD34 alone can markedly inhibit cell growth as a consequence of apoptosis (Lord et al., 1990. Nucl. Acids Res. 18:2823; Grishin et al., 2001, Proc. Natl. Acad. Sci. U.S.A. 98:10172-10177; Hollander et al., 2003, Oncogene 22:3827-3832; Hollander et al., 2001, Int. J. Cancer 96:22-31; Hollander et al., 1997, J. Biol. Chem. 272: 13731-13737). The amino-terminal third of the GADD34 protein is involved in augmentation of apoptosis following ionizing radiation (Lord et al., 1990. Nucl. Acids Res. 18:2823). In human, mouse, hamster and rat, GADD34 protein contains 674, 657, 590 and 577 amino acids, respectively (Fornace et al., 1989, Mol. Cell Bio. 9:4196-4203; Hollander et al., 2003, Oncogene 22:3827-3832; Hollander et al., 1997, J. Biol. Chem. 272:13731-13737; Lord et al., 1990. Nucl. Acids Res. 18:2823; Zhan et al., 1994, Mol. Cell Biol. 14:2361-2371). GADD34 protein contains a series of repeated sequences in the central region. These repeats are 34, 40 and 39 amino acids long for human, mouse, hamster and rat GADD34 proteins, respectively (Bulavin et al., 1999, EMBO J. 18:6845-6854; Chou et al., 1994, Proc. Natl. Acad. Sci. U.S.A. 91:5247-5251). The human protein has four copies of the repeat sequence, while the mouse, hamster and rat protein has 4.5, 3.5 and 2.5 copies, respectively (Hollander et al., 2003, Oncogene 22:3827-3832; Hollander et al., 1997, J. Biol. Chem. 272:13731-13737). In rodents the repeat sequences are arranged in tandem, while in humans these repeats are separated by varying numbers of amino acids. The functional significance of these repeats is unclear. Approximately 90 amino acids at the carboxy-terminal end of GADD34 protein are highly conserved across species, with approximately 90 percent amino acid homology.

Recent cloning of rat GADD34 revealed that PEG-3 is identical to rat GADD34 in the first 415 amino acids (Hollander et al., 2003, Oncogene 22:3827-3832; Su et al., 1997, Proc. Natl. Acad. Sci. U.S.A. 95:14400-14405). A single base deletion resulted in frame-shift and premature appearance of stop codon resulting in C-terminal truncation and sequence divergence of PEG-3 from rat GADD34 (Su et al., 1997, Proc. Natl. Acad. Sci. U.S.A. 95:14400-14405). Southern blot analysis showed that there is a single locus for GADD34 in the normal rat genome suggesting, that PEG-3, a mutated form of GADD34, might be generated during the process of transformation and tumor progression (Hollander et al., 2003, Oncogene 22:3827-3832).

3. SUMMARY OF THE INVENTION

The present invention relates to chimeric molecules comprising portions of rat PEG-3 ("rPEG-3") and human GADD34 ("hGADD34") having apoptotic activity. It is based, at least in part, on the discovery that a chimeric protein comprising amino acids 1-347 of rat PEG-3 fused with residues 418-674 of human GADD34 exhibited anti-proliferative activity when expressed in transformed cells. The present invention provides for this and other rPEG3/hGADD34 chimeras, and the use of such proteins in inhibiting cell proliferation, angiogenesis, and tumor growth.

4. BRIEF DESCRIPTION OF THE DRAWINGS

FIG. 1A-D. Schematic representations of mutations in rGADD34 in the context of transformation of rat cells. The numbers on top denote the position of the nucleic acid in the open reading frame (ORF). A. Rat GADD34 ORF showing oligonucleotide subsequences (SEQ ID NO:13; SEQ ID NO:14; and SEQ ID NO:15). The underlined and bold base is deleted in PEG-3. B. ORF of PEG-3 showing oligonucleotide subsequences (SEQ ID NO:16) and mutated GADD34 from RT2 and 4E11 cells. C. ORF of mutated GADD34 showing oligonucleotide subsequences (SEQ ID NO:17) from C6 cells. The underlined and bold base is inserted. D. ORF of mutated GADD34 from CREF cells. The underlined and bold base is inserted. D. ORF of mutated GADD34 showing oligonucleotide subsequences (SEQ ID NO:18) from CREF cells. The underlined and bold base is inserted.

Figure 2:
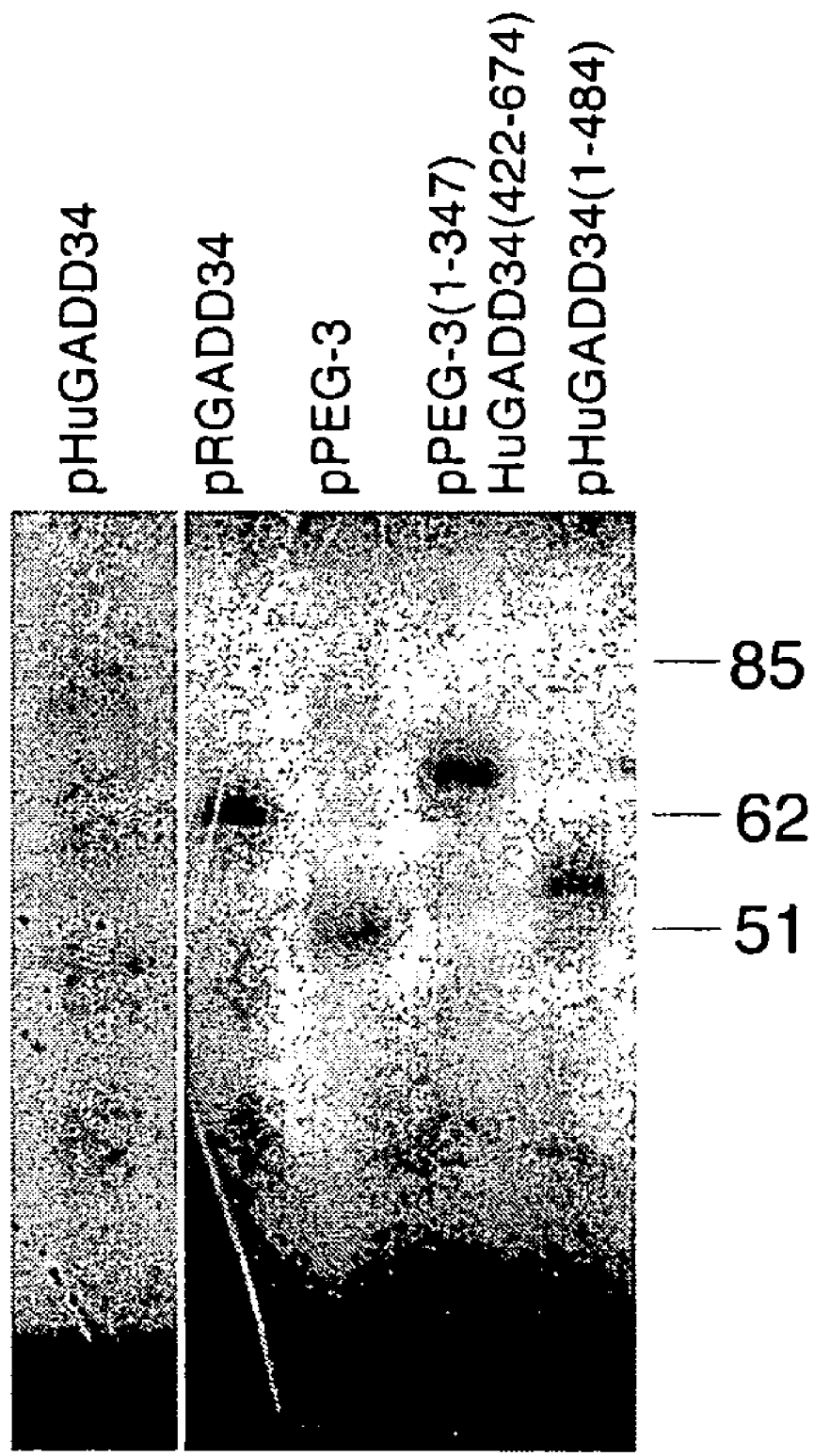

FIG. 2. Engineered plasmids make authentic proteins. In vitro translation was performed with the indicated plasmid constructs as described in materials and methods. The numbers on the left denote the sizes of the molecular weight markers in kDa.

Figure 3:
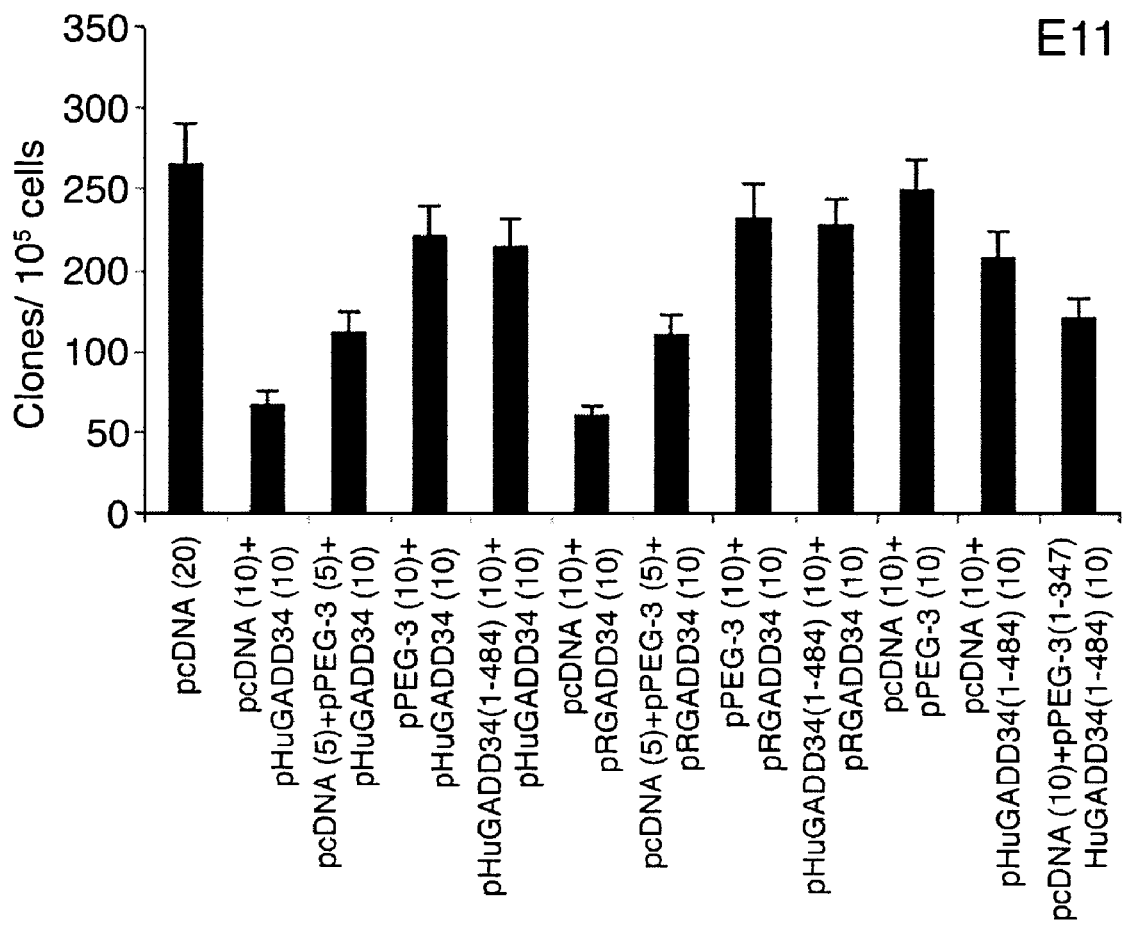

FIG. 3. PEG-3 functions as a dominant negative of growth suppression by GADD34 in E11 cells. The indicated plasmid constructs were transfected in E11 cells and growth was analyzed by clonogenic survival assays. pcDNA represents empty pcDNA3.1/Hygro(+) vector and the numbers 5, 10 and 20 in parentheses represent μg of DNA used for transfection. The data represent mean±S.D. of three independent experiments each performed in triplicates.

Figure 4:
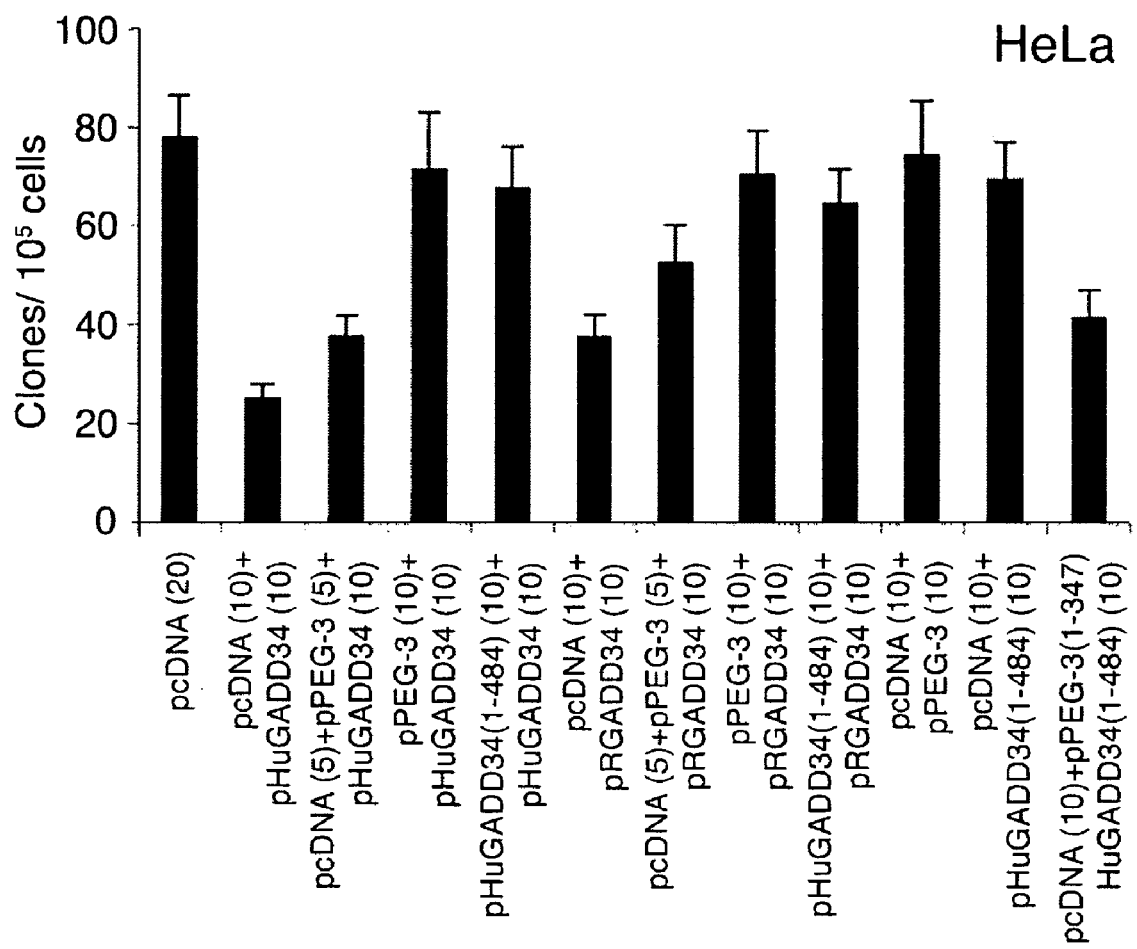

FIG. 4. PEG-3 functions as a dominant negative of growth suppression by GADD34 in HeLa cells. The indicated plasmid constructs were transfected in HeLa cells and growth was analyzed by clonogenic survival assays. pcDNA represents empty pcDNA3.1/Hygro(+) vector and the numbers 5, 10 and 20 in parentheses represent μg of DNA used for transfection. The data represent mean±S.D. of three independent experiments each performed in triplicates.

Figure 5:
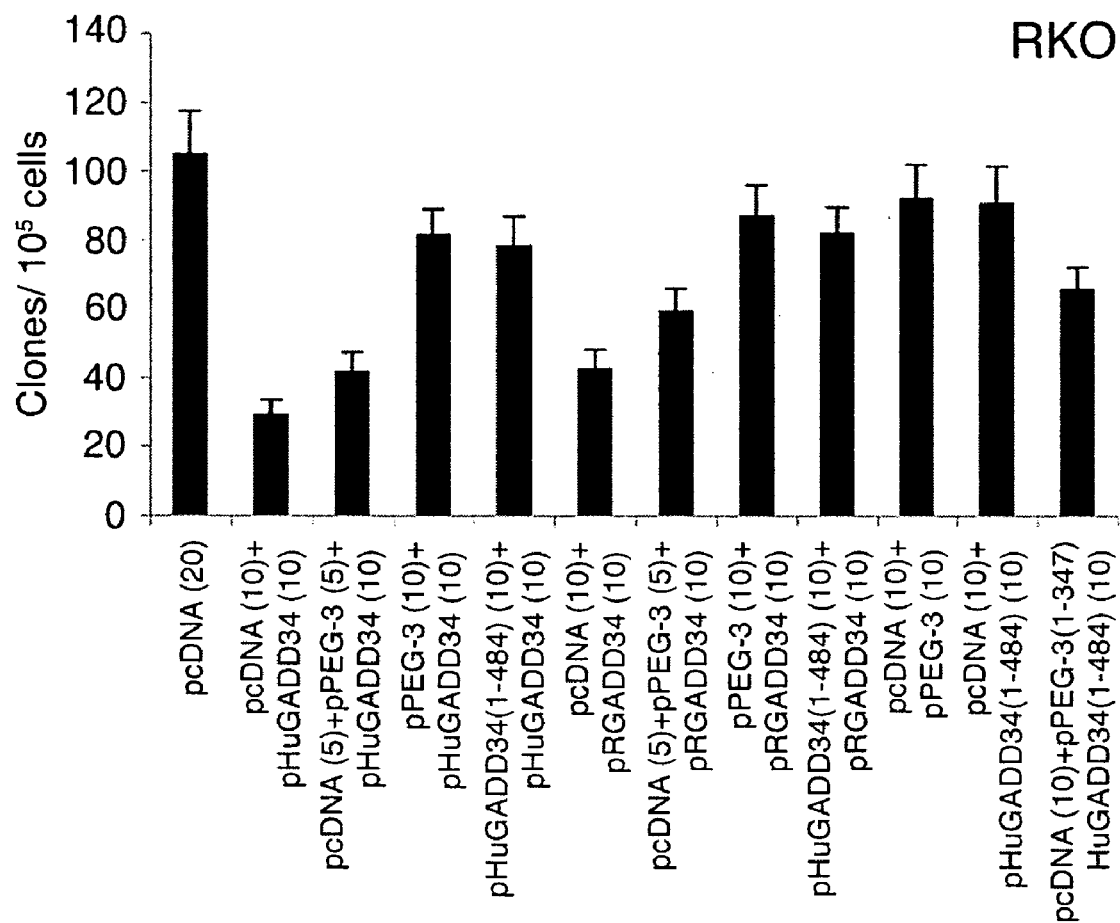

FIG. 5. PEG-3 functions as a dominant negative of growth suppression by GADD34 in RKO cells. The indicated plasmid constructs were transfected in RKO cells and growth was analyzed by clonogenic survival assays. pcDNA represents empty pcDNA3.1/Hygro(+) vector and the numbers 5, 10 and 20 in parentheses represent μg of DNA used for transfection. The data represent mean±S.D. of three independent experiments each performed in triplicates.

Figure 6:
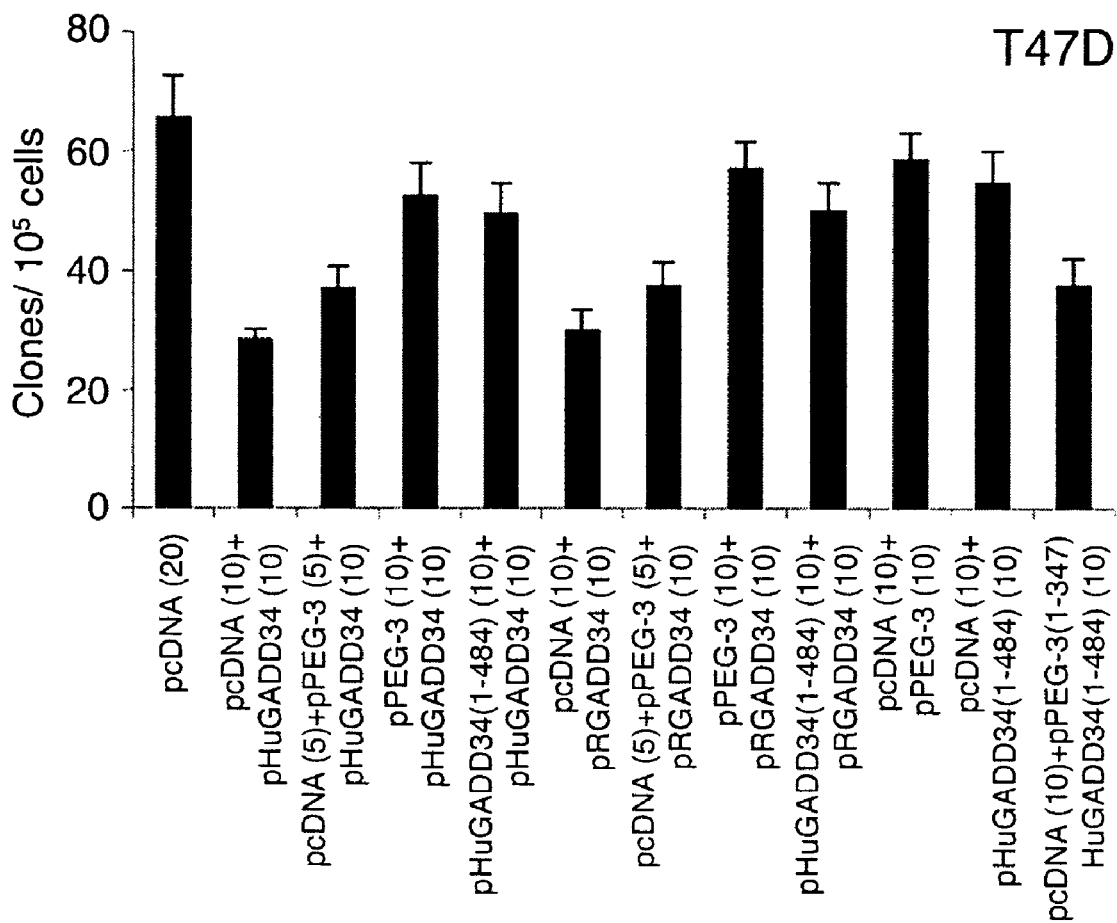

FIG. 6. PEG-3 functions as a dominant negative of growth suppression by GADD34 in T47D cells. The indicated plasmid constructs were transfected in T47D cells and growth was analyzed by clonogenic survival assays. pcDNA represents empty pcDNA3.1/Hygro(+) vector and the numbers 5, 10 and 20 in parentheses represent μg of DNA used for transfection. The data represent mean±S.D. of three independent experiments each performed in triplicates.

Figure 7:
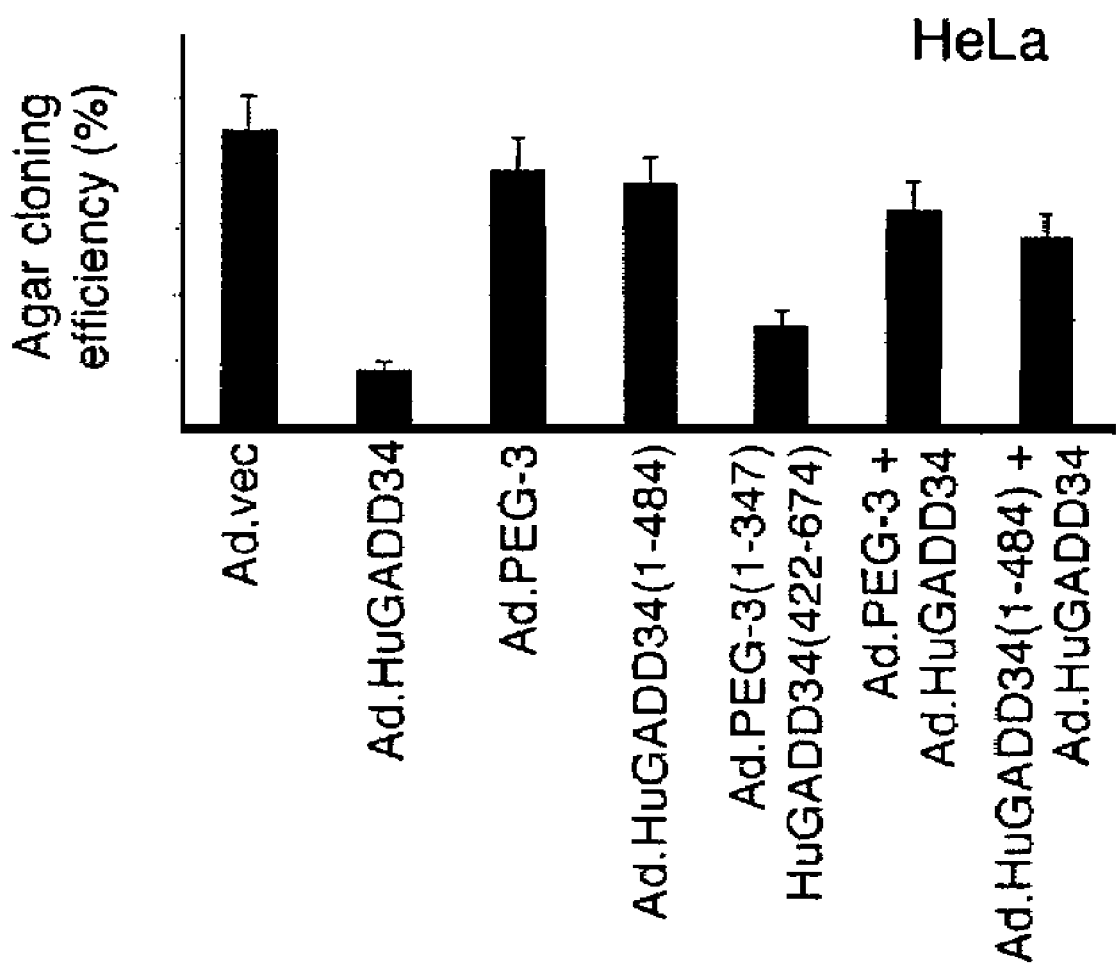

FIG. 7. Ad.PEG-3 is a dominant negative of growth inhibition by Ad.HuGADD34. HeLa cells were infected with the indicated Ad as described in the text and growth was analyzed by clonogenic survival assays. The data represent mean±S.D. of three independent experiments each performed in triplicates.

Figure 8:
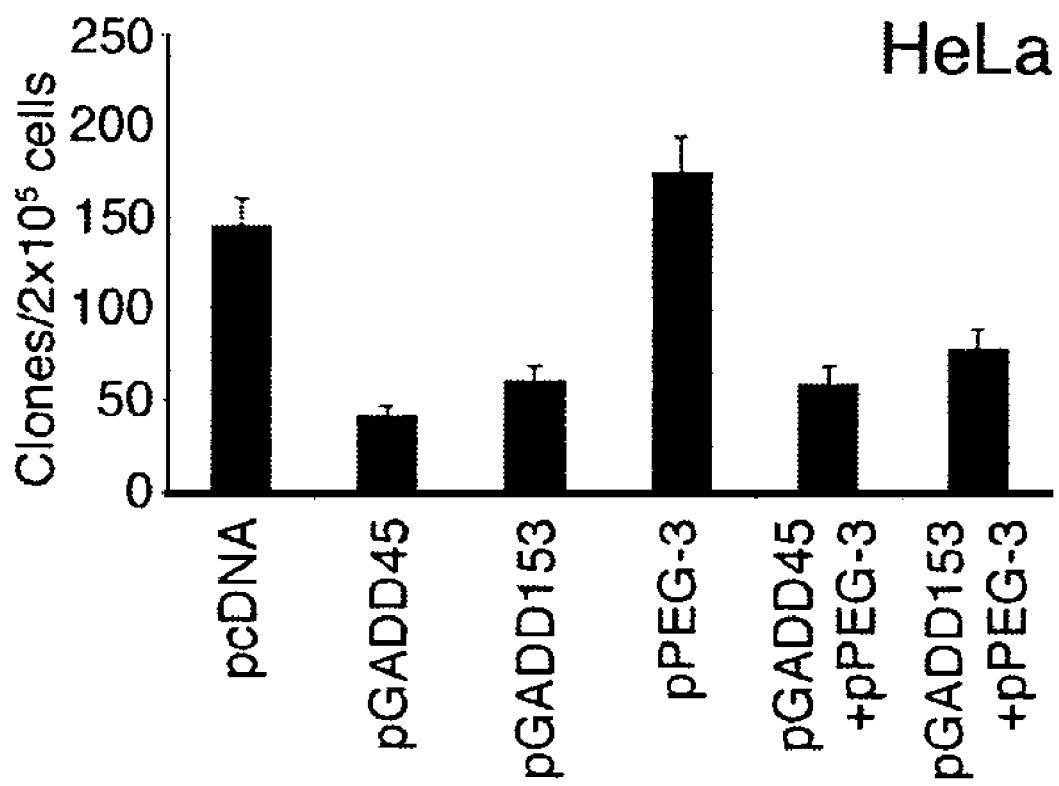

FIG. 8. PEG-3 functions as a dominant negative of GADD34 but not of GADD45 or GADD153. The indicated plasmid constructs were transfected in HeLa cells and growth was analyzed by clonogenic survival assays. pcDNA represents empty pcDNA3.1/Hygro(+) vector. The data represent mean±S.D. of three independent experiments each performed in triplicates.

Figure 9:
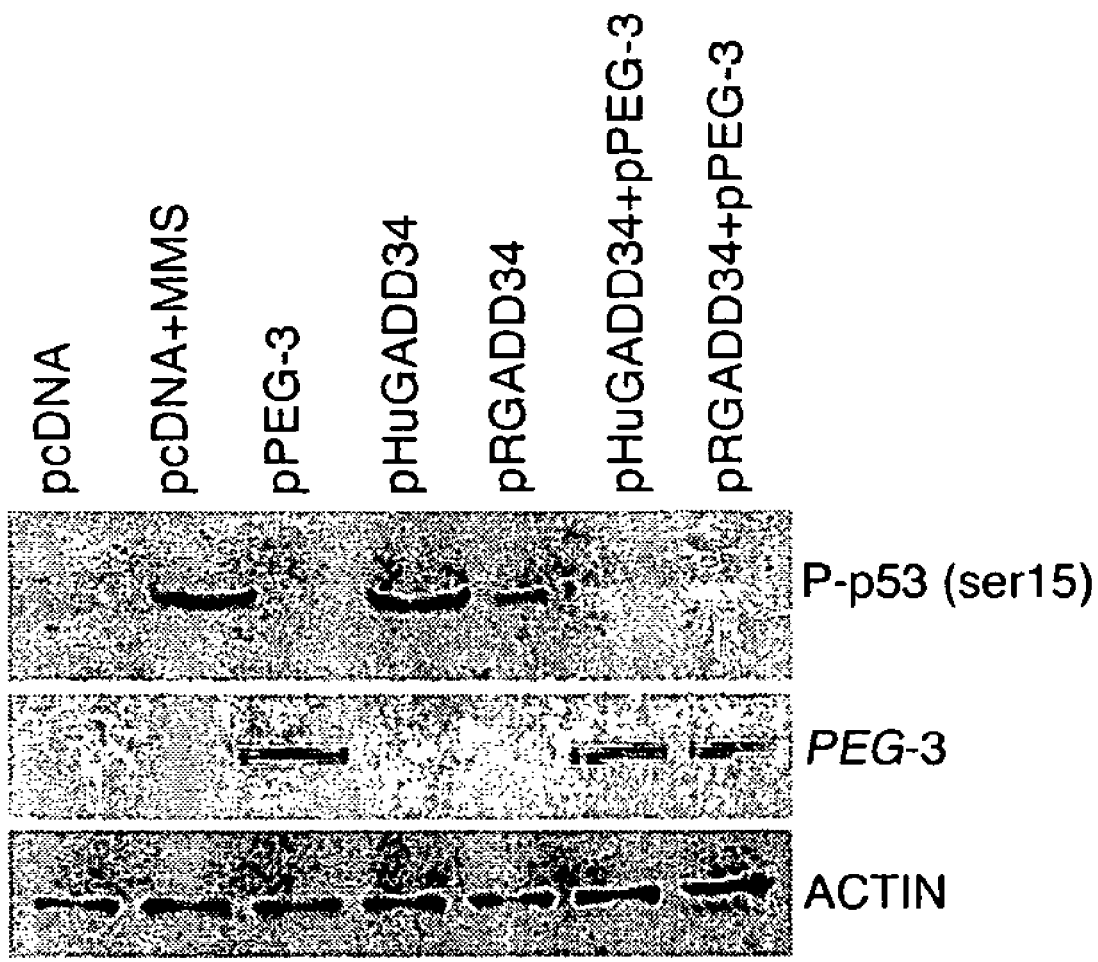

FIG. 9. PEG-3 inhibits GADD34-induced phosphorylation of p53. SaOS2 cells were transfected with pC53-C1N3 in combination with the indicated plasmid constructs and phosphorylated p53 was analyzed by Western blot analysis. pcDNA: empty pcDNA3.1/Hygro(+) vector, MMS: methyl methanesulfonate.

Figure 10:
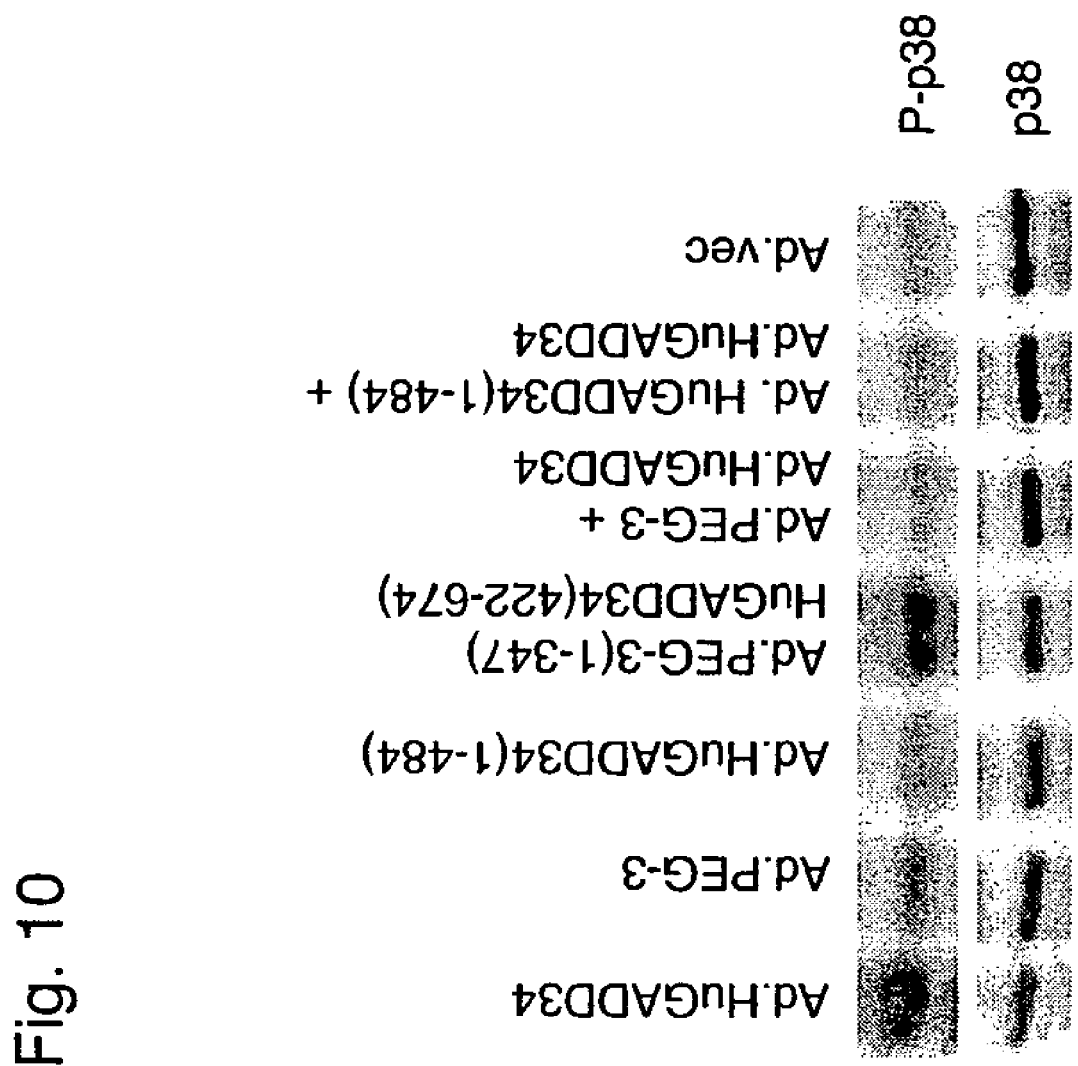

FIG. 10. PEG-3 inhibits GADD34-induced p38 MAPK phosphorylation. Hela cells were infected with the indicated Ad and phospho- and total p38 MAPK were analyzed by Western blot analysis.

Figure 11:
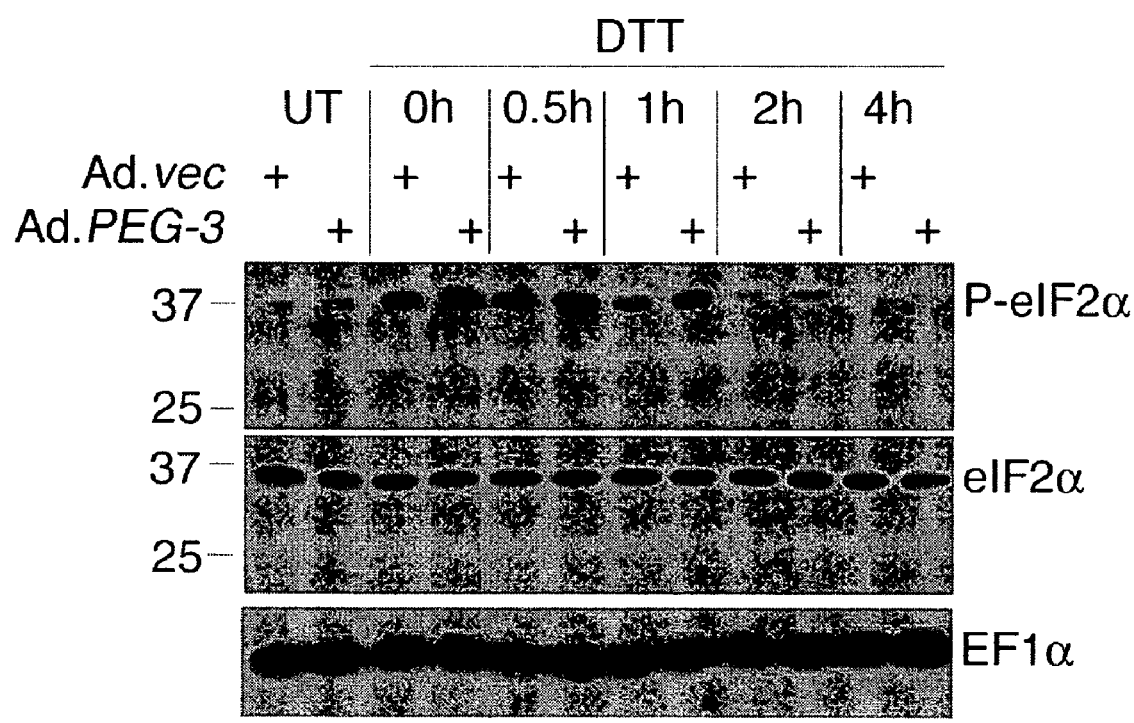

FIG. 11. PEG-3 does not inhibit GADD34-mediated eIF2α dephosphorylation. HeLa cells were infected with either Ad.vec or Ad.PEG-3 at an m.o.i. of 50 pfu/cell. 48 hr later cells were treated with DTT as described in materials and methods. Cells were harvested at the indicated time points and the expressions of the indicated proteins were analyzed by Western blot analysis.

FIG. 12. Amino acid sequence of r PEG-3 (SEQ ID NO:1, from GenBank AF020618).

FIG. 13. Amino acid sequence of hGADD34 (SEQ ID NO:2; from GenBank U83981).

FIG. 14. Nucleic acid sequence of rPEG-3 (SEQ ID NO:3; from GenBank AF020618).

FIG. 15. Nucleic acid sequence of hGADD34 (SEQ ID NO:4, from GenBank U83981).

FIG. 16. Amino acid sequence of a rPEG-3/hGADD34 chimera (SEQ ID NO:5)

FIG. 17. Nucleic acid sequence encoding the rPEG-3/hGADD34 chimeric protein of FIG. 16 (SEQ ID NO:6)

SEQUENCE LISTING

The specification further incorporates by reference the Substitute Sequence Listing submitted herewith via EFS on Jun. 11, 2008. Pursuant to 37 C.F.R. § 1.52(e)(5), the Sequence Listing text file, identitied as 0700502617seqlist2.TXT, is 25,889 bytes and was created on May 13, 2008. The Substitute Listing, electronically filed herewith, does not extend beyond the scope of the specificaton and thus does not contain new matter.

5. DETAILED DESCRIPTION OF THE INVENTION

For purposes of clarity, and not by way of limitation, the detailed description of the invention is divided into the following subsections:

(1) rPEG-3/hGADD34 chimeric proteins;

(2) nucleic acids encoding rPEG-3/hGADD34 chimeric proteins; and (3) uses of the invention.

5.1 rPEG-3/hGADD34 Chimeric Proteins

The present invention provides for chimeric proteins comprising an N-terminal portion comprising rPEG-3 amino acid sequences and a C-terminal portion comprising hGADD34 amino acid sequences. The complete amino acid sequences of rPEG-3 and hGADD34 are set forth as SEQ ID NOS: 1 and 2, respectively, having GenBank Accession Numbers of AF020618 for rPEG-3 and U83981 for hGADD34. The numbering of amino acid residues herein refers to the amino acid sequences as set forth in SEQ ID NOS:1 and 2.

In various non-limiting embodiments, the N-terminal portion comprises at least amino acid residues 1-270 of rPEG-3, and the C-terminal portion comprises at least amino acid residues 510-674 of hGADD34, where the N-terminal and C-portions are linked, optionally with a linker molecule between. "At least" means that additional rPEG-3 and/or human GADD34, respectively, amino acid sequence may be incorporated into molecules of the invention. Preferably the N-terminal and C-terminal portions are linked by an amide bond, but other forms of linkage are envisaged by the invention. A linker molecule may be a peptide or peptidomimetic sequence. The linker molecule may comprise portions having amino acid sequences occurring in rPEG-3 and/or hGADD34, or may comprise a different sequence, such as a functionally irrelevant and/or inactive sequence, which may contain repetitive elements. In non-limiting embodiments the linker may be between 10 and 50, between 50 and 100, between 100 and 150, or between 150 and 200 amino acid residues in length.

In one specific non-limiting embodiment, the chimeric protein comprises a N-terminal portion comprising amino acid residues 1-270 of rPEG-3, and a C-terminal portion comprising amino acid residues 510-674 of hGADD34, where the N-terminal and C-portions are linked, optionally by a linker molecule comprising between 10 and 50 amino acids, which may or may not comprise one or more amino acid sequence which is a subsequence of the amino acid sequence of rPEG-3 (SEQ ID NO:1) or human GADD34 (SEQ ID NO:2).

In another specific non-limiting embodiment, the chimeric protein comprises a N-terminal portion comprising amino acid residues 1-270 of rPEG-3, and a C-terminal portion comprising amino acid residues 510-674 of hGADD34, where the N-terminal and C-portions are linked, optionally by a linker molecule comprising between 50 and 100 amino acids, which may or may not comprise one or more amino acid sequence which is a subsequence of the amino acid sequence of rPEG-3 (SEQ ID NO:1) or human GADD34 (SEQ ID NO:2).

In yet another specific non-limiting embodiment, the chimeric protein comprises a N-terminal portion comprising amino acid residues 1-270 of rPEG-3, and a C-terminal portion comprising amino acid residues 510-674 of hGADD34, where the N-terminal and C-portions are linked, optionally by a linker molecule comprising between 100 and 150 amino acids, which may or may not comprise one or more amino acid sequence which is a subsequence of the amino acid sequence of rPEG-3 (SEQ ID NO:1) or human GADD34 (SEQ ID NO:2).

In yet another specific non-limiting embodiment, the chimeric protein comprises a N-terminal portion comprising amino acid residues 1-270 of rPEG-3, and a C-terminal portion comprising amino acid residues 510-674 of hGADD34, where the N-terminal and C-portions are linked, optionally by a linker molecule comprising between 150 and 200 amino acids, which may or may not comprise one or more amino acid sequence which is a subsequence of the amino acid sequence of rPEG-3 (SEQ ID NO:1) or human GADD34 (SEQ ID NO:2).

In various non-limiting embodiments, a chimeric protein comprises amino acid residues 1-270, 1-280, 1-290, 1-300, 1-310, 1-320, 1-330, 1-340, 1-350, 1-360, 1-370, 1-380, 1-390, 1-400, 1-410, 1-411, 1-412, 1-413, 1-414, 1-415, 1-416, 1-417, 1-418, 1-419 or 1-420 amino acids of rPEG-3 sequence, with 0-5 amino acids omitted at each end, linked, optionally via a linker molecule, to residues 510-674, 500-674, 490-674, 480-674, 470-674, 460-674, 450-674, 440-674, 430-674, 420-674, 418-674, or 410-674 of hGADD34, with 0-5 amino acids omitted at each end. Preferably, but not by way of limitation, a chimeric protein comprises an N-terminus comprising a rPEG-3 amino acid sequence beginning at a residue between residue 1 and residue 10 in the rPEG-3 sequence and ending at a residue between residue 300 and residue 375 of rPEG-3, or a molecule at least 90 (and preferably at least 95) percent homologous thereto, linked, optionally via a linker molecule, to a C terminus comprising a hGADD34 amino acid sequence beginning between residue 410 and residue 480 and ending at a residue between 664 and 674 of hGADD34, or a molecule at least 90 (and preferably at least 95) percent homologous thereto.

In a preferred, specific non-limiting embodiment, the present invention provides for a chimeric protein comprising amino acid residues 1-347 of rPEG-3 linked, optionally via a linker, to amino acid residues 418-674 of hGADD34. One such protein is exemplified in Section 6 below, and has amino acid SEQ ID NO:5.

The present invention further provides for an aforementioned chimeric protein, for use in preparing a pharmaceutical composition which may be used to inhibit cell proliferation, induce apoptosis, inhibit tumor growth, decrease a population of cancer cells, or treat a subject suffering from a cancer or other disorder of cell proliferation.

The present invention provides for pharmaceutical compositions comprising an effective amount of one of the aforementioned chimeric proteins in a suitable carrier, said proteins may be comprised in a delivery means such as, but not limited to, a liposome, a microsphere or a nanoparticle.

5.2 Nucleic Acids Encoding rPEG-3/hGADD34 Chimeric Proteins

The present invention provides for nucleic acid molecules that encode the chimeric proteins set forth in the preceding section. Such nucleic acid molecules may be prepared synthetically or using genetic engineering techniques. A person skilled in the art would readily be able to prepare nucleic acid molecules encoding the above-recited chimeric proteins, either using materials available in the art or FIGS. 12 and 13 herein, which show the amino acid sequences of rPEG-3 and hGADD34 respectively (which are SEQ ID NOs: 1 and 2, respectively), and/or FIGS. 14 and 15, which depict the nucleic acid sequences of rPEG-3 and hGADD34 (SEQ ID NOS:3 and 4, respectively). Further, suitable nucleic acid sequences may be deduced based on the genetic code.

A nucleic acid molecule encoding a specific non-limiting embodiment of the invention, the chimeric protein exemplified in Section 6, below, is set forth as SEQ ID NO:6. The present invention further provides for nucleic acid molecules that hybridize to a nucleic acid sequence as set forth in SEQ ID NO:6 or its complementary strand under stringent conditions, and also provides for nucleic acids that are at least 90 percent or at least 95 percent homologous to the sequence set forth in SEQ ID NO:6, as determined using standard homology-determining software such as BLAST or FASTA. Stringent conditions for detecting hybridization of nucleic acid molecules are set forth in "Current Protocols in Molecular Biology", Vol. 1, Ausubel et al., eds. John Wiley: New York N.Y., pp. 2.10.1-2.10.16, first published in 1989 but with annual updating, wherein maximum hybridization specificity for DNA samples immobilized on nitrocellulose filters may be achieved through hybridization to filter-bound DNA or RNA in 0.5 M NaHPO4, 7% sodium dodecyl sulfate (SDS), 1 mM EDTA at 65° C., and washing twice or more in 0.1×SSC (15-30 mM NaCl, 1.5-3 mM sodium citrate, pH 7.0)/0.1% SDS at 68° C. For DNA or RNA samples immobilized on nylon filters, a stringent hybridization washing solution may alternatively be comprised of 40 mM NaPO4, pH 7.2, 1-2% SDS and 1 mM EDTA, for which a washing temperature of at least 65-68° C. is recommended.

A nucleic acid encoding a chimeric rPEG-3/hGADD34 protein of the invention may be operably linked to a promoter element and optionally additional elements that facilitate expression. Suitable promoters include constitutively active promoters, selectively active promoters, and inducible promoters. Suitable promoters include, but are not limited to, the cytomegalovirus immediate early promoter, the Rous sarcoma virus long terminal repeat promoter, the human elongation factor-1α promoter, the human ubiquitin c promoter, etc. (Colosimo et al., 2000, Biotechniques 29(2):314-318, 320-322, 324) and the PEG-3 promoter (U.S. Pat. Nos. 6,472, 520 and 6,737,523; Su et al., 2000, Oncogene 19:3411-3421; Su et al., 2001, Nucleic Acids Res 29:1661-1671). It may be desirable, in certain embodiments of the invention, to use an inducible promoter. Non-limiting examples of inducible promoters include the murine mammary tumor virus promoter (inducible with dexamethasone); commercially available tetracycline-responsive or ecdysone-inducible promoters, etc. (Romano, 2004, Drug News Perspect 17(2):85-90). In specific non-limiting embodiments of the invention, the promoter may be selectively active in cancer cells, such as the prostate specific antigen gene promoter (O'Keefe et al., 2000, Prostate 45:149-157), the kallikrein 2 gene promoter (Xie et al., 2001, Human Gene Ther 12:549-561), the human alpha-fetoprotein gene promoter (Ido et al., 1995, Cancer Res 55:3105-3109), the c-erbB-2 gene promoter (Takakuwa et al., 1997, Jpn. J. Cancer Res. 88:166-175), the human carcinoembryonic antigen gene promoter (Lan et al., 1996, Gastroenterol. 111:1241-1251), the gastrin-releasing peptide gene promoter (Inase et al., 2000, Int. J. Cancer 85:716-719), the human telomerase reverse transcriptase gene promoter (Pan and Koenman, 1999, Med Hypotheses 53:130-135), the hexokinase II gene promoter (Katabi et al., 1999, Human Gene Ther 10:155-164), the L-plastin gene promoter (Peng et al., 2001, Cancer Res 61:4405-4413), the neuron-specific enolase gene promoter (Tanaka et al., 2001, Anticancer Res 21:291-294), the midkine gene promoter (Adachi et al., 2000, Cancer Res 60:4305-4310), the human mucin gene MUC1 promoter (Stackhouse et al., 1999, Cancer Gene Ther 6:209-219), and the human mucin gene MUC4 promoter (Genbank Accession No. AF241535), which is particularly active in pancreatic cancer cells (Perrais et al., 2000, J Biol Chem 276(33):30923-30933).

Nucleic acid molecules of the invention, including nucleic acids operably linked to promoter elements and/or other expression enhancing elements, may be comprised in a suitable vector molecule, such as a plasmid, phage, phagemid, virus, or mini-chromosome.

In non-limiting embodiments, a nucleic acid molecule encoding a chimeric rPEG-3/hGADD34 protein, optionally operably linked to a promoter element and/or other expression-enhancing elements, may be comprised in an expression vector. Suitable expression vectors include, but are not limited to, virus-based vectors and non-virus based DNA or RNA delivery systems. Examples of appropriate virus-based gene transfer vectors include, but are not limited to, those derived from retroviruses, for example Moloney murine leukemia-virus based vectors such as LX, LNSX, LNCX or LXSN (Miller and Rosman, 1989, Biotechniques 7:980-989); lentiviruses, for example human immunodeficiency virus ("HIV"), feline leukemia virus ("FIV") or equine infectious anemia virus ("EIAV")-based vectors (Case et al., 1999, Proc. Natl. Acad. Sci. U.S.A. 96: 22988-2993; Curran et al., 2000, Molecular Ther. 1:31-38; Olsen, 1998, Gene Ther. 5:1481-1487; U.S. Pat. Nos. 6,255,071 and 6,025,192); adenoviruses (Zhang, 1999, Cancer Gene Ther. 6(2):113-138; Connelly, 1999, Curr. Opin. Mol. Ther. 1(5):565-572; Stratford-Perricaudet, 1990, Human Gene Ther. 1:241-256; Rosenfeld, 1991, Science 252:431-434; Wang et al., 1991, Adv. Exp. Med. Biol. 309:61-66; Jaffe et al., 1992, Nat. Gen. 1:372-378; Quantin et al., 1992, Proc. Natl. Acad. Sci. U.S.A. 89:2581-2584; Rosenfeld et al., 1992, Cell 68:143-155; Mastrangeli et al., 1993, J. Clin. Invest. 91:225-234; Ragot et al., 1993, Nature 361:647-650; Hayaski et al., 1994, J. Biol. Chem. 269:23872-23875; Bett et al., 1994, Proc. Natl. Acad. Sci. U.S.A. 91:8802-8806), for example Ad5/CMV-based E1-deleted vectors (Li et al., 1993, Human Gene Ther. 4:403-409); adeno-associated viruses, for example pSub201-based AAV2-derived vectors (Walsh et al., 1992, Proc. Natl. Acad. Sci. U.S.A. 89:7257-7261); herpes simplex viruses, for example vectors based on HSV-1 (Geller and Freese, 1990, Proc. Natl. Acad. Sci. U.S.A. 87:1149-1153); baculoviruses, for example AcMNPV-based vectors (Boyce and Bucher, 1996, Proc. Natl. Acad. Sci. U.S.A. 93:2348-2352); SV40, for example SVluc (Strayer and Milano, 1996, Gene Ther. 3:581-587); Epstein-Barr viruses, for example EBV-based replicon vectors (Hambor et al., 1988, Proc. Natl. Acad. Sci. U.S.A. 85:4010-4014); alphaviruses, for example Semliki Forest virus- or Sindbis virus-based vectors (Polo et al., 1999, Proc. Natl. Acad. Sci. U.S.A. 96:4598-4603); vaccinia viruses, for example modified vaccinia virus (MVA)-based vectors (Sutter and Moss, 1992, Proc. Natl. Acad. Sci. U.S.A. 89:10847-10851) or any other class of viruses that can efficiently transduce human tumor cells and that can accommodate the nucleic acid sequences required for therapeutic efficacy.

Non-limiting examples of non-virus-based delivery systems which may be used according to the invention include, but are not limited to, so-called naked nucleic acids (Wolff et al., 1990, Science 247:1465-1468), nucleic acids encapsulated in liposomes (Nicolau et al., 1987, Methods in Enzymology 1987:157-176), nucleic acid/lipid complexes (Legendre and Szoka, 1992, Pharmaceutical Research 9:1235-1242), and nucleic acid/protein complexes (Wu and Wu, 1991, Biother. 3:87-95).

The present invention further provides for a pharmaceutical composition comprising one of the aforementioned chimeric protein-encoding nucleic acids, optionally comprised in a vector, in a suitable pharmaceutical carrier. In specific non-limiting embodiments, the nucleic acid may be comprised in a liposome, microsphere, microparticle, or nanoparticle.

The present invention further provides for an aforementioned chimeric protein-encoding nucleic acid for use in preparing a pharmaceutical composition which may be used to inhibit cell proliferation, induce apoptosis, inhibit tumor growth, decrease a population of cancer cells, or treat a subject suffering from a cancer or other disorder of cell proliferation.

The present invention provides for pharmaceutical compositions comprising an effective amount of an aforementioned nucleic acid (optionally contained in a vector) in a suitable pharmaceutical carrier.

5.3 Uses of the Invention

A chimeric protein according to the invention may be administered to a target cell directly, or may be introduced into the target cell by introducing, into said cell, a nucleic acid molecule encoding the chimeric protein, in expressible form. Suitable target cells include undesirable cells and cells, the proliferation of which is desired to be inhibited. Examples of target cells include but are not limited to cancer cells, including breast cancer, lung cancer (non-small cell, small cell, large cell and mesothelioma), liver cancer, leukemia, lymphoma (Hodgkins and Non-Hodgkins), gastric cancer, pancreatic cancer, duodenal cancer, colon cancer, rectal cancer, ovarian cancer, testicular cancer, prostate cancer, uterine cancer, sarcoma, fibrosarcoma, astroscarcoma, glioblastoma, and melanoma cells, as well as vascular endothelial cells.

Targeting of chimeric protein may be achieved, for example, by creating a fusion protein which combines the chimeric protein with a targeting molecule, such as an antibody or receptor ligand.

Targeting of chimeric protein-encoding nucleic acid may be achieved using targeting vector molecules or by use of a promoter to drive chimeric protein expression where the promoter is selectively active in the target cell. For example, but not by way of limitation, suitable promoter elements include the rPEG-3 promoter (U.S. Pat. Nos. 6,472,520 and 6,737, 523, Su et al., 2000, Oncogene 19:3411-3421 and Su et al., 2001, Nucleic Acids Res 29:1661-1671); the prostate specific antigen gene promoter (O'Keefe et al., 2000, Prostate 45:149-157), the kallikrein 2 gene promoter (Xie et al., 2001, Human Gene Ther 12:549-561), the human alpha-fetoprotein gene promoter (Ido et al., 1995, Cancer Res 55:3105-3109), the c-erbB-2 gene promoter (Takakuwa et al., 1997, Jpn. J. Cancer Res. 88:166-175), the human carcinoembryonic antigen gene promoter (Lan et al., 1996, Gastroenterol. 111:1241-1251), the gastrin-releasing peptide gene promoter (Inase et al., 2000, Int. J. Cancer 85:716-719), the human telomerase reverse transcriptase gene promoter (Pan and Koenman, 1999, Med Hypotheses 53:130-135), the hexokinase 11 gene promoter (Katabi et al., 1999, Human Gene Ther 10:155-164), the L-plastin gene promoter (Peng et al., 2001, Cancer Res 61:4405-4413), the neuron-specific enolase gene promoter (Tanaka et al., 2001, Anticancer Res 21:291-294), the midkine gene promoter (Adachi et al., 2000, Cancer Res 60:4305-4310), the human mucin gene MUC1 promoter (Stackhouse et al., 1999, Cancer Gene Ther 6:209-219), and the human mucin gene MUC4 promoter (Genbank Accession No. AF241535), which is particularly active in pancreatic cancer cells (Perrais et al., 2000, J Biol Chem 276(33):30923-30933).

Accordingly, the present invention provides for a method for inducing apoptosis in a target cell comprising introducing, into the target cell, a chimeric protein of the invention (in the form of protein itself or a nucleic acid encoding the protein, in expressible form (that is, where the nucleic acid is operably linked to a suitable promoter element)).

The present invention further provides for a method for inhibiting proliferation of a target cell comprising introducing, into the target cell, a chimeric protein of the invention (in the form of protein itself or a nucleic acid encoding the protein, in expressible form).

The present invention further provides for a method of inhibiting angiogenesis, comprising introducing, into a target vascular endothelial cell, a chimeric protein of the invention (in the form of protein itself or a nucleic acid encoding the protein, in expressible form).

The present invention further provides for a method of treating a cancer in a subject, comprising introducing, into a cancer cell of the subject, a chimeric protein of the invention (in the form of protein itself or a nucleic acid encoding the protein, in expressible form).

The present invention further provides for a method for inhibiting the growth of a tumor in a subject, comprising introducing, into the tumor (tumor cells and/or vascular endothelial cells) a chimeric protein of the invention (in the form of protein itself or a nucleic acid encoding the protein, in expressible form).

6. EXAMPLE: A PEG3/GADD34 CHIMERA

6.1 Materials and Methods

Cell Lines and Culture Conditions. CREF is a specific clone of Fischer F2408 rat embryo fibroblast cells (Fisher et al., 1982). CREF-ras, CREF-src and CREF-A2 are stable clones of CREF, modified by transfection to express dominant acting oncogenes, HA-ras, v-src, or a specific mutant of Ad5 (H5hr1), respectively (Su et al., 1993, 1994, 1997). E11 is a single cell clone of mutant Ad5 (H5ts125)-transformed Sprague-Dawley secondary rat embryo cells (Fisher et al., 1978). RT2, C6 and 9L are rat gliomas, 4E11 is a rat hepatocarcinoma and UMR106 is a rat osteosarcoma cell line. HeLa is a human cervical carcinoma, RKO is a human colorectal carcinoma, T47D is a human breast carcinoma and SaOS2 is a human osteosarcoma cell line. All cultures were grown in Dulbecco's modified Eagle's medium (DMEM) supplemented with 5% FBS (DMEM-5) at 37° C. in a humidified 5% $CO_2$/95% air incubator.

Construction of Plasmids and Transfection. All expression plasmids were constructed in pcDNA3.1/Hygro(+) (Invitrogen, Carlsbad, Calif.). The plasmids pHuGADD34, pRGADD34, pPEG-3, pGADD45 and pGADD153 contain the complete open reading frames of human GADD34, rat GADD34, PEG-3, human GADD45 and human GADD153 genes, respectively. pHuGADD34(1-484), that expresses amino acid 1-484 of human GADD34, was created by PCR using pHuGADD34 as template and primers sense: 5' ATG GCC CCA GGC CAA GCA 3' (SEQ ID NO:7) and antisense: 5' AGG TCA ATA TCC CCA GCC 3' (SEQ ID NO:8). pPEG-3(1-347)HuGADD34(418-674), that expresses amino acids 1-347 of PEG-3 fused with amino acids 418-674 of human GADD34, was created by artificially creating an MluI site in huGADD34 by PCR using primers sense: 5' GAC GCG TTG ACT TCT GCT 3, (SEQ ID NO:9) and antisense: 5' TCA GCC ACG CCT CCC ACT 3, (SEQ ID NO:10). The MluI-digested PCR fragment was ligated with MluI-digested pPEG-3 to make the PEG-3/human GADD34 fusion construct. pC53-C1N3 expresses wild-type p53 and contains exons 2-11 and introns 2-4 of p53 gene in the vector pCMV-NEO-BAM (Hinds et al., 1990). $10^6$ cells per dish were plated in 100 mm dishes and transfection was carried out next day using Lipofectamine 2000 (Invitrogen) transfection reagent and 20 μg of plasmid DNA according to the manufacturer's instructions.

Construction of adenoviruses and infection protocol The recombinant replication-incompetent adenovirus (Ad) expressing PEG-3 (Ad.PEG-3) was produced as previously described (Su et al., 1999). Ads expressing HuGADD34 (Ad.HuGADD34), HuGADD34(1-484) [Ad.HuGADD34(1-484)] and PEG-3(1-347)HuGADD34(418-674) [Ad.PEG-3(1-347)HuGADD34(418-674)] were created in two steps as described previously and plaque purified by standard procedures (Su et al., 1999; Valerie, 1999). As a control empty replication incompetent adenovirus (Ad.vec) was used. Cells were infected with a multiplicity of infection (m.o.i.) of 50 plaque forming units (pfu)/cell of different Ads as described (Valerie, 1999).

Clonogenic Survival Assay. Two days after transfection, cells were trypsinized, counted and $10^5$ cells per dish were re-plated in 60-mm dishes and selected in the presence of hygromycin. After two weeks, colonies were fixed with 4% formaldehyde and stained with a 5% (w/w) solution of Geimsa stain in water. Colonies>50 cells were counted.

Anchorage Independent Growth Assay. Six hours after adenoviral infection, cells were trypsinized, counted and $10^5$ cells per dish were allowed to grow in 0.8% soft agar in 60-mm dishes. After two weeks, colonies>50 cells were counted and scored.

In Vitro Translation. In vitro translation was performed using pHuGADD34, pRGADD34, pPEG-3, pHuGADD34 (1-486) and pPEG-3(1-347)HuGADD34(418-674) as templates and TNT coupled reticulocyte lysate systems (Promega, Madison, Wis.) according to the manufacturer's protocol. The in vitro translation products were electrophoresed by SDS-PAGE and visualized by autoradiography.

RNA Extraction, RT-PCR and Sequencing. Total RNA was extracted as described previously (Su et al., 1998) and cDNA was synthesized using superscript II reverse transcriptase (Invitrogen). PCR was performed using the RT product as template and primers, sense: 5' TGA GAC TTC TGT CTG TTC 3' (SEQ ID NO:11) and antisense: 5' TGG CTT CTG TCC AGG TAA 3' (SEQ ID NO:12) to amplify 813-1275-bp of the coding sequence. The PCR product was cloned by T-A cloning into pCR2.1 vector (Invitrogen) and sequenced using M13 forward and reverse primers.

Western Blotting. The levels of phosphorylated p53, PEG-3, total and phosphorylated p38 MAPK and actin proteins were determined by Western blot analysis as described (Su et al., 1998). Cells were harvested in RIPA buffer (0.5 M NaCl/ 0.5% Nonidet P-40/20 mM Tris, pH 8.0/1 mM phenylmethylsulfonyl fluoride). The protein levels were then determined by Western blotting by enhanced chemiluminescence (Amersham) with an anti-phospho-p53 (Ser 15) antibody (Cell signaling technology), anti-PEG-3 peptide-derived rabbit polyclonal antibody (Santa Cruz Biotechnology, Santa Cruz, Calif.), anti-p38 MAPK and anti-phospho-p38 MAPK (Cell signaling technology), and an anti-actin mAb (Santa Cruz).

Endoplasmic Reticulum (ER) Stress and Analysis of eIF2α Phosphorylation. HeLa cells were infected with either Ad.vec or Ad.PEG-3. 48 hr later, the cells were treated with 10 mM dithiothreitol (DTT; Sigma) for 30 min. The medium was replaced and the cells were harvested in RIPA buffer containing 1 mM $Na_3VO_4$ and 50 mM NaF at intervals. Expressions of phosphorylated eIF2α, total eIF2α and EF1α were analyzed by Western blot analysis. The primary antibodies used were anti-eIF2α [$pS^{52}$] (rabbit; Biosource International; Camarillo, Calif.; 1:1000); anti-eIF2α (mouse; Biosource; 1:1000) and EF1α (mouse; Upstate Biotechnology, Waltham, Mass.).

Statistical Analysis. All the experiments were performed at least three times. The results are expressed as mean±S.D. Statistical comparisons were made using an unpaired two-tailed Student's 1-test. A $p<0.05$ was considered as significant.

6.2 Results

Mutation in the GADD34 gene is a frequent event during transformation of rat cells. The rGADD34 cDNA has an open reading frame (ORF) of 1731-bp (Hollander et al., 2003). PEG-3 is generated by deletion of a guanine base at position 1246 in the ORF of rGADD34 (considering the translation start site of rGADD34 as position 1) resulting in frame-shift and premature appearance of a stop-codon that truncates the ORF to 1371-bp (Su et al., 1997). Since PEG-3 promotes multiple changes that aid tumor progression (Su et al., 1999, 2002) and it was cloned from E11, a mutant Ad5 (H5ts125)-transformed rat embryo cell clone that form slow, compact tumors, it was hypothesized that during the process of transformation and/or immortalization of rat cells, rGADD34 might be mutated to generate PEG-3 and this mutation might be important to induce transformation and/or immortalization. To address this issue, rGADD34 cDNA was sequenced in a number of rat tumor cell lines and immortalized rat embryo fibroblast cells (FIG. 1). Attention was focused on the region that showed the 1-bp deletion in PEG-3. Total RNA was purified and RT-PCR was performed using primers that amplify 813-1275-bp of the rGADD34 ORF. The PCR fragments were cloned and sequenced. The rGADD34 cDNA was cloned from primary rat hepatocytes and this sequence was identical to that of the published rGADD34 sequence. Of direct relevance to the hypothesis that PEG-3 is a mutated form of rGADD34, the same deletion was identified in rGADD34, as was observed in PEG-3 cloned from E11 cells, in two additional rat tumor cell lines, namely RT2, a malignant glioma cell line and 4E11, a hepatocarcinoma cell line. In the C6 rat glioma cell line, insertion of a cytosine at position 1079 led to a frame-shift and premature stop-codon resulting in a protein containing 377-aa, which is identical to rGADD34 in the first 359-aa. In 9L malignant glioma and UMR106 osteosarcoma cell lines no mutation was detected in this region of the rGADD34 gene. We also checked the rGADD34 sequence in CREF (a clonal population of immortal normal Fischer rat embryo fibroblasts) and its transformed derivatives, such as C REF-ras, CREF-src and CREF-A2. In these cell lines there was a one base insertion at position 826 that resulted in frame-shift and premature appearance of a stop-codon truncating the ORF of rGADD34 to 897-bp. This generates a protein of 299-aa that is identical to rGADD34 in the first 275-aa. These findings clearly document that during transformation and/or immortalization of rat cells the rGADD34 gene is frequently mutated generating C-terminally truncated proteins.

PEG-3 functions as a dominant negative of GADD34-mediated growth inhibition. Experiments were performed to understand and determine the significance of the generation of PEG-3 in the contexts of GADD34 function. For this purpose, two constructs were generated, pHuGADD34(1-484) and pPEG-3(1-347)HuGADD34(418-674), the former lacks the C-terminal region of HuGADD34, thus resembling PEG-3, the latter has the C-terminal region of HuGADD34 fused to the N-terminal of PEG-3, thus resembling GADD34, to determine if such a construct can restore GADD34 function. In vitro translation was used to check for the authenticity of these constructs. All the constructs generated proteins the sizes of which corresponded to that predicted from the deduced amino acid residues (FIG. 2) indicating the authenticity of the constructs. pHuGADD34, pRGADD34, pPEG-3, pPEG-3(1-347)HuGADD34(418-674) and pHuGADD34(1-484) generated proteins of 73.5-, 63-, 50-, 66- and 53-kDa, respectively.

pHuGADD34, pRGADD34, pPEG-3, pHuGADD34(1-484) and pPEG-3(1-347)HuGADD34(418-674) were transfected into E11, HeLa, RKO and T47D cell lines either alone or in combination and the clonogenic survival of the cells was assessed (FIGS. 3, 4, 5, and 6). Transfection of pPEG-3 or pHuGADD34(1-484) alone had little or no significant inhibitory effect on cell growth in any of the cell types tested (FIGS. 3, 4, 5 and 6; lanes 10 and 11). Transfection of either pHuGADD34 or pRGADD34 in E11 cells, reduced their colony formation ability to ~31% and ~28%, respectively, when the colony formation ability of empty pcDNA3.1/Hygro(+)-transfected cells was regarded as 100% (FIG. 3). Co-transfection of pPEG-3 resulted in a dose-dependent protection against both HuGADD34- and rGADD34-induced growth inhibition. Co-transfection of 5 and 10 μg of pPEG-3 increased the colony formation ability to ~52% and ~80% and ~51% and ~87% in the presence of 10 μg of pHuGADD34 and pRGADD34, respectively. Similarly co-transfection of 10 μg of pHuGADD34(1-484) increased the colony formation ability to ~77% and ~83% in the presence of pHuGADD34 and pRGADD34, respectively. Transfection of pPEG-3(1-347)HuGADD34(418-674) reduced the colony formation ability to ~56%.

Similar findings were observed when the constructs were evaluated in human tumor cells. In HeLa cells, transfection of either pHuGADD34 or pRGADD34 reduced their colony forming ability to 3.2% and ~48%, respectively (FIG. 4). Co-transfection of pPEG-3 provided dose-dependent protection, increasing the colony formation ability to ~92% and ~90% with the maximum dose, in the presence of pHuGADD34 and pRGADD34, respectively. Co-transfection of pHuGADD34(1-484) with pHuGADD34 and pRGADD34 increased the colony formation ability to ~87% and ~83%, respectively. pPEG-3(1-347)HuGADD34(418-674) reduced the colony forming ability to ~53%.

pHuGADD34 and pRGADD34 reduced the colony forming ability of RKO cells to ~27% and ~41%, respectively, which was increased to ~78% and ~83%, respectively, by a maximum dose of pPEG-3 (FIG. 5). Co-transfection of pHuGADD34(1-484) with pHuGADD34 or pRGADD34 increased the colony formation ability to ~75% and ~78%, respectively. pPEG-3(1-347)HuGADD34(418-674) reduced the colony formation ability to ~62%.

In T47D cells, transfection of pHuGADD34 and pRGADD34 reduced the colony forming ability to ~44% and ~46%, respectively, that was rescued to ~80% and ~87%, respectively, by pPEG-3 and ~76% and ~77%, respectively, by pHuGADD34(1-484) (FIG. 6). pPEG-3(1-347)HuGADD34(418-674) reduced the colony forming ability to ~57%.

The findings of the transfection studies were further confirmed by infecting HeLa cells with replication incompetent adenoviruses (Ads), Ad.PEG-3, Ad.HuGADD34, Ad.HuGADD34(1-484) and Ad.PEG-3(1-347)HuGADD34 (418-674) in different combinations and analyzing the anchorage independent growth of the cells in soft agar (FIG. 7). The multiplicity of infection (m.o.i.) was always kept constant at 100 pfu/cell. Thus, for the control empty adenovirus (Ad.vec) the m.o.i. was 100 pfu/cell, for a single transgene-expressing Ad the m.o.i. was 50 pfu/cell+50 pfu/cell of Ad.vec and for two transgene-expressing adenoviruses the m.o.i. was 50 pfu/cell for each Ad. Infection with Ad.HuGADD34 reduced the agar cloning efficiency of HeLa cells by ~81% compared to infection with Ad.vec. Co-infection of Ad.PEG-3 or Ad.HuGADD34(1-484) with Ad.HuGADD34 rescued the cells from Ad.HuGADD34mediated growth inhibition so that the agar cloning efficiency was decreased by only ~27% and ~36%, respectively. Infection with Ad.PEG-3 or Ad.HuGADD34(1-484) alone did not affect the agar cloning efficiency significantly, while infection with Ad.PEG-3(1-347)HuGADD34 (418-674) reduced colony formation in agar by ~66%. All these findings indicate that PEG-3 and HuGADD34(1-484), that resembles PEG-3, are potent inhibitors of the growth suppressive properties of both human and rat GADD34. Additionally, fusing PEG-3 with the C-terminal region of GADD34, so that it resembles GADD34, results in significant restoration of its growth inhibitory property.

To determine the specificity of the dominant negative action of PEG-3 towards GADD34, pGADD45 or pGADD153 were transfected into HeLa cells in the absence or presence of pPEG-3 and analyzed the colony formation ability. Both pGADD45 and pGADD153 showed potent growth suppression properties (FIG. 8). However, pPEG-3 failed to rescue the cells from this growth inhibition confirming the specificity of PEG-3 to GADD34-induced growth inhibitory function.

Although it is well established that GADD34 induces growth arrest predominantly by apoptosis, the molecular mechanism of its apoptosis-inducing effect remains to be elucidated. A recent report indicated that GADD34 induces p53 phosphorylation in serine 15 (Yagi et al., 2003). Phosphorylated p53 is a potent mediator of apoptosis (Fiscella et al., 1993). pC53-C1N3, which expresses wild-type p53, was transfected into the human osteosarcoma cell line SaOS2, which is null for p53. As a positive control, it was confirmed that the DNA damaging agent MMS induces phosphorylation of p53 (FIG. 9). Transfection of pHuGADD34 or pRGADD34 resulted in increased phosphorylated p53 while co-transfection of pPEG-3 reversed GADD34-induced p53 phosphorylation. Transfection of pPEG-3 alone did not induce p53 phosphorylation. These findings indicate that the dominant negative effect of PEG-3 over the growth inhibitory properties of GADD34 might be mediated by the inhibitory effect of PEG-3 towards GADD34-induced p53 phosphorylation.

p38 MAPK has been shown to be involved in phosphorylation of p53 in serine 15 (Bulavin et al.; 1999; She et al., 2000, 2001). Therefore, the activation of p38 MAPK by GADD34 was determined. As shown in FIG. 10, infection of HeLa cells with Ad.HuGADD34 or Ad.PEG-3(1-347) HuGADD34(418-674) significantly increased phospho-p38 MAPK in comparison to infection with Ad.vec (lanes 1, 4 and 7). Infection of Ad.PEG-3 or Ad.HuGADD34(1-484) completely inhibited Ad.HuGADD34-induced p38 MAPK phosphorylation (lanes 5 and 6) although these two adenoviruses alone did not affect the basal level of phospho-p38 MAPK (lanes 2 and 3). The total p38 MAPK level was unchanged under any experimental condition. These findings indicate that GADD34 activates p38 MAPK pathway, which is inhibited by PEG-3 and this pathway might be involved in GADD34-induced p53 phosphorylation.

PEG-3 does not inhibit GADD34-induced eIF2α dephosphorylation. During ER stress eIF2α is phosphorylated and GADD34 is induced. The function of GADD34 is to dephosphorylate eIF2α thus facilitating early recovery from a prolonged state of translational inhibition (Kojima et al., 2003; Novoa et al., 2001). It was determined whether PEG-3 functions as a dominant negative for the eIF2α dephosphorylation function of GADD34 during ER stress. HeLa cells were infected with Ad.PEG-3 and 48 hr later the cells were treated for 30 min with 10 mM DTT, which induces ER stress by disrupting disulfide bond formation, after which the medium was replaced. The cells were harvested at intervals and the expression level of phosphorylated eIF2α and total eIF2α was analyzed. As shown in FIG. 11, treatment with DTT resulted in a significant level of phosphorylation of eIF2α in both Ad.vec- and Ad.PEG-3-infected cells until 2 hr post-DDT-treatmentment and by 4 hr the level of phosphorylated eIF2α returned to basal level in both samples indicating that PEG-3 could not prevent the dephosphorylation of eIF2α by GADD34. The levels of total eIF2α and the housekeeping protein EF1α remained unchanged in all the samples.

6.3 Discussion

Carcinogenesis is a complex process, which is multi-factorial in terms of its etiology and multi-step in its evolution. One important mechanism of tumor formation is the deregulation of cell growth regulatory genes, most importantly inactivation of negative regulators of cell growth (Sherr, 2004). The classical example is the inactivation of p53 or Retinoblastoma (Rb) proteins that lead to the generation of diverse types of tumors (Sherr & McCormick, 2002). As a DNA damage-inducible gene (Fornace et al., 1989), the primary function of GADD34 might be to induce apoptotic cell death in DNA-damaged cells so that these cells do not by-pass cellular growth regulatory controls and acquire independent proliferative abilities. In these contexts, inactivation of GADD34 might serve as an essential component in the intricate process of transformation, tumor initiation and progression. To date, no direct evidence has been identified linking GADD34 inactivation to tumorigenesis. The observation that HRX-fusion proteins are generated during acute leukemia and these fusion proteins, but not wild-type HRX proteins, can inhibit GADD34-mediated apoptosis suggests that functional inactivation of GADD34 by HRX-fusion proteins might be a potential mechanism of leukemia pathogenesis (Adler et al., 1999). The results set forth above show that mutation, such as insertions or deletions, in the GADD34 gene occurs as a frequent event during transformation/immortalization and/or progression in rodent cells. In diverse types of rat tumors, C-terminal truncations of GADD34 protein are generated that are either identical to PEG-3 or are structurally similar to it. These mutations are early events during the process of transformation because mutation in rGADD34 was detected in parental CREF cells, which are immortal but not tumorigenic (Fisher et al., 1982).

By clonogenic survival and anchorage independent growth assays PEG-3 was shown to be a dominant negative inhibitor of GADD34. Additionally, it was previously demonstrated that PEG-3 expression alone in transformed and tumor-derived cells can enhance the process of tumor progression by modulating genomic stability, invasion and angiogenesis (Su et al., 1999, 2002). These findings support the hypothesis that either the inhibition of wild-type GADD34 by PEG-3 or PEG-3-like molecules (when one allele of the GADD34 gene is mutationally inactivated) or facilitation of cell growth by PEG-3 itself (either in mono- or bi-allelic inactivation) might be a crucial event in rodent tumorigenesis. This raises the interesting question of whether this type of genetic change also occurs in humans. Our preliminary studies aimed at sequencing the human GADD34 gene in a number of human cancer cells revealed no PEG-3-like mutations indicating that unlike rodents, mutational inactivation of the GADD34 gene might not be a frequent event during human carcinogenesis. However, functional inactivation of GADD34 by protein-protein interactions or inactivation of expression by mutation in the promoter region could provide alternate mechanisms for a role of GADD34 in human tumor formation. Using colony formation assays in RKO cells a recent report suggested that co-transfection of a C-terminal truncated HuGADD34 did not rescue HuGADD34-mediated growth inhibition (Hollander et al., 2003). However, in the expanded and more detailed assays in both rodent and multiple human cell lines, including RKO, described herein, both PEG-3 and C-terminal truncations of HuGADD34 provided protection against both HuGADD34 and rGADD34-mediated growth inhibition. The reason for this discrepancy is not apparent but might be explained by technical issues such as quality of the constructs generated and transfection methodology affecting transfection efficiency.

GADD34 is a multi-functional protein. It induces apoptosis, while also functioning as a component of the negative feedback loop that facilitates the ability of a cell to overcome prolonged translational inhibition as a consequence of unfolded protein response (UPR) (Kojima et al., 2003; Novoa et al., 2001). The C-terminal region of GADD34, that interacts with PP1α and thus allows dephosphorylation of eIF2α, is important for this function. Experiments were performed to determine whether PEG-3 can also function as a dominant negative inhibitor of the dephosphorylation function of GADD34. Interestingly, overexpression of PEG-3 did not prolong the phosphorylated eIF2α (FIG. 5) indicating that PEG-3 specifically interferes with the growth-suppressing function of GADD34, rather than being a global inhibitor of all GADD34-induced functions. The N-terminal region of GADD34 has been implicated as a relevant molecule involved in its apoptosis-inducing properties (Adler et al., 1999). It is possible that PEG-3 might bind and squelch a yet-to-be identified protein that interacts with the N-terminal region of GADD34, which is crucial in mediating GADD34-induced apoptosis. Identification of such a protein would be crucial for comprehending exactly how GADD34 functions as an apoptosis-inducing gene.

6.4 References

Adler et al., 1999, Mol. Cell Biol. 19: 7050-60.
Babiss et al., 1985,. Science 228:1099-101.
Brush et al., 2003, Mol. Cell. Biol. 23:1292-303.
Bulavin et al., 1999,. Embo J. 18: 6845-54.
Chou et al., 1995, Proc. Natl. Acad. Sci. U.S.A. 92: 10516-20.
Chou & Roizman, 1994, Proc. Natl. Acad. Sci. U.S.A. 91:5247-51.
Connor et al., 2001,. Mol. Cell Biol. 21: 6841-50.
Fiscella et al., 1993, Oncogene 8: 1519-28.
Fisher et al., 1982, Proc. Natl. Acad. Sci. U.S.A. 79: 3527-31.
Fisher et al., 1978, Proc. Natl. Acad. Sci. U.S.A. 75: 2311-4.
Fornace et al., 1989, Mol. Cell Biol. 9: 4196-203.
Grishin et al., 2001, Proc. Natl. Acad. Sci. U.S.A. 98: 10172-7.
Hasegawa & Isobe, 1999,. Biochim Biophys Acta 1428: 161-8.
Hasegawa et al., 2000a,. Biochem. J. 352 Pt 3: 795-800.
Hasegawa et al., 2000b, Biochem. Biophys. Res. Commun. 267: 593-6.
He et al., 1996,. J. Virol. 70: 84-90.
He et al., 1997, Proc. Natl. Acad. Sci. U.S.A. 94: 843-8.
Hinds et al., 1990, Cell Growth Differ. 1: 571-80.
Hollander et al., 2003, Oncogene 22: 3827-32.
Hollander et al., 2001, Int. J. Cancer 96: 22-31.
Hollander et al., 1997, J. Biol. Chem. 272: 13731-7.
Kojima et al., 2003, Faseb J. 17: 1573-5.
Lord et al., 1990,. Nucleic Acids Res. 18: 2823.
Novoa et al., 2001,. J. Cell Biol. 153: 1011-22.
Sarkar et al., 2002,. Proc. Natl. Acad. Sci. U.S.A. 99: 10054-9.
She et al., 2001, Cancer Res. 61:1604-10.
She et al., 2000, J. Biol. Chem. 275: 20444-9.
Sherr, 2004, Cell, 116: 235-46.
Sherr & McCormick, 2002, Cancer Cell 2: 103-12.
Shi et al., 2004, J. Cell Biol. 164: 291-300.
Su et al., 1993, Oncogene 8: 1211-9.
Su et al., 1999, Proc. Natl. Acad. Sci. U.S.A. 96: 15115-20.
Su et al., 2002, J. Cell Physiol. 192: 34-44.
Su et al., 1994, Cancer Res. 54: 1865-70.
Su et al., 1998, Proc. Natl. Acad. Sci. U.S.A. 95: 14400-5.
Su et al., 1997, Proc. Natl. Acad. Sci. U.S.A. 94: 9125-30.
Takekawa & Saito, 1998, Cell 95: 521-30.
Valerie, 1999, Biopharmaceutical Drug Design and Development. Humana press: Totowa, N.J., pp 69-142.
Yagi et al., 2003, J. Cell Biochem. 90: 1242-9.
Zhan et al., 1994, Mol. Cell Biol. 14: 2361-71.

Various publications are cited herein, the contents of which are hereby incorporated by reference in their entireties.

I claim:

1. A nucleic acid molecule encoding a chimeric protein which inhibits cell prolifertion having an N-terminal portion and a C-terminal portion, wherein the N-terminal portion comprises at least amino acid residues 1-270 of rPEG-3 (SEQ ID NO:1) and the C-terminal portion comprises at least amino acid residues 510-674 of hGADD34 (SEQ ID NO:2).

2. The nucleic acid molecule of claim 1, wherein the N-terminal and C-terminal portions of the encoded chimeric protein are linked via a peptide linker molecule.

3. A nucleic acid molecule encoding a chimeric protein which inhibits cell proliferation having an N-terminal portion and a C-terminal portion, wherein the N-terminal portion comprises a rPEG-3 amino acid sequence beginning at a residue between residue 1 and residue 10 and ending at a residue between residue 300 and residue 375 of rPEG-3 amino acid sequence (SEQ ID NO:1) and the C-terminal portion comprises a hGADD34 amino acid sequence beginning between residue 410 and residue 480 and ending at a residue between 664 and 674 of hGADD34 amino acid sequence (SEQ ID NO:2).

4. The nucleic acid molecule of claim 3 wherein the N-terminal and C-terminal portions of the encoded chimeric protein are linked via a peptide linker molecule.

5. The nucleic acid molecule of claim 3 wherein the N-terminal portion of the encoded chimeric protein comprises amino acid residues 1-347 of rPEG-3 (SEQ ID NO:1 ) and the C-terminal portion comprises amino acid residues 418-674 of hGADD34 (SEQ ID NO:2) wherein at least a leucine residue is located between said amino acid 347 of rPEG-3 (SEQ ID NO:1 ) and said residue 418 of hGADD34 (SEQ ID NO:2).

6. The nucleic acid molecule of claim 5, wherein the amino acid sequence of the encoded protein is (SEQ ID NO:5).

7. The nucleic acid molecule of claim 5 wherein the N-terminal and C-terminal portions of the encoded chimeric protein are linked via a peptide linker molecule.

* * * * *

SEQUENCE LISTING

<160> NUMBER OF SEQ ID NOS: 12

<210> SEQ ID NO 1
<211> LENGTH: 457
<212> TYPE: PRT
<213> ORGANISM: Rattus
<220> FEATURE:
<223> OTHER INFORMATION: rat PEG-3 amino acid sequence

<400> SEQUENCE: 1

```
Met Ala Pro Ser Pro Arg Pro Gln His Val Leu His Trp Lys Glu Ala
 1               5                  10                  15

His Ser Phe Tyr Leu Leu Ser Pro Leu Met Gly Phe Leu Ser Arg Ala
            20                  25                  30

Trp Ser Arg Leu Arg Gly Pro Glu Val Ser Glu Ala Trp Leu Ala Glu
        35                  40                  45

Thr Val Ala Gly Ala Asn Gln Ile Glu Ala Asp Ala Leu Leu Thr Pro
    50                  55                  60

Pro Pro Val Ser Glu Asn His Leu Pro Leu Arg Glu Thr Glu Gly Asn
65                  70                  75                  80

Gly Thr Pro Glu Trp Ser Lys Ala Ala Gln Arg Leu Cys Leu Asp Val
                85                  90                  95

Glu Ala Gln Ser Ser Pro Pro Lys Thr Trp Gly Leu Ser Asp Ile Asp
            100                 105                 110

Glu His Asn Gly Lys Pro Gly Gln Asp Gly Leu Arg Glu Gln Glu Val
        115                 120                 125

Glu His Thr Ala Gly Leu Pro Thr Leu Gln Pro Leu His Leu Gln Gly
    130                 135                 140

Ala Asp Lys Lys Val Gly Glu Val Val Ala Arg Glu Glu Gly Val Ser
145                 150                 155                 160

Glu Leu Ala Tyr Pro Thr Ser His Trp Glu Gly Pro Ala Glu Asp
                165                 170                 175

Glu Glu Asp Thr Glu Thr Val Lys Lys Ala His Gln Ala Ser Ala Ala
            180                 185                 190

Ser Ile Ala Pro Gly Tyr Lys Pro Ser Thr Ser Val Tyr Cys Pro Gly
        195                 200                 205

Glu Ala Glu His Arg Ala Thr Glu Glu Lys Gly Thr Asp Asn Lys Ala
    210                 215                 220

Glu Pro Ser Gly Ser His Ser Arg Val Trp Glu Tyr His Thr Arg Glu
225                 230                 235                 240

Arg Pro Lys Gln Glu Gly Glu Thr Lys Pro Glu Gln His Arg Ala Gly
                245                 250                 255

Gln Ser His Pro Cys Gln Asn Ala Glu Ala Glu Gly Gly Pro Glu
            260                 265                 270

Thr Ser Val Cys Ser Gly Ser Ala Phe Leu Lys Ala Trp Val Tyr Arg
        275                 280                 285

Pro Gly Glu Asp Thr Glu Glu Glu Asp Ser Asp Leu Asp Ser Ala
    290                 295                 300

Glu Glu Asp Thr Ala His Thr Cys Thr Thr Pro His Thr Ser Ala Phe
305                 310                 315                 320

Leu Lys Ala Trp Val Tyr Arg Pro Gly Glu Asp Thr Glu Glu Glu Asp
                325                 330                 335

Asp Gly Asp Trp Asp Ser Ala Glu Glu Asp Ala Ser Gln Ser Cys Thr
            340                 345                 350
```

```
Thr Pro His Thr Ser Ala Phe Leu Lys Ala Trp Val Tyr Arg Pro Gly
        355                 360                 365

Glu Asp Thr Glu Glu Asp Ser Glu Asn Val Ala Pro Val Asp
        370                 375                 380

Ser Glu Thr Val Asp Ser Cys Gln Ser Thr Gln His Cys Leu Pro Val
385                 390                 395                 400

Glu Lys Thr Lys Gly Cys Gly Glu Ala Glu Pro Pro Phe Gln Trp
                    405                 410                 415

Pro Ser Ile Tyr Leu Asp Arg Ser Gln His His Leu Gly Leu Pro Leu
                420                 425                 430

Ser Cys Pro Phe Asp Cys Arg Ser Gly Ser Asp Leu Ser Lys Pro Pro
            435                 440                 445

Pro Gly Ile Arg Ala Leu Arg Phe Leu
        450                 455

<210> SEQ ID NO 2
<211> LENGTH: 674
<212> TYPE: PRT
<213> ORGANISM: Homo sapien
<220> FEATURE:
<223> OTHER INFORMATION: human GADD34 amino acid sequence

<400> SEQUENCE: 2

Met Ala Pro Gly Gln Ala Pro His Gln Ala Thr Pro Trp Arg Asp Ala
1               5                   10                  15

His Pro Phe Phe Leu Leu Ser Pro Val Met Gly Leu Leu Ser Arg Ala
                20                  25                  30

Trp Ser Arg Leu Arg Gly Leu Gly Pro Leu Glu Pro Trp Leu Val Glu
            35                  40                  45

Ala Val Lys Gly Ala Ala Leu Val Glu Ala Gly Leu Glu Gly Glu Ala
        50                  55                  60

Arg Thr Pro Leu Ala Ile Pro His Thr Pro Trp Gly Arg Arg Pro Glu
65                  70                  75                  80

Glu Glu Ala Glu Asp Ser Gly Gly Pro Gly Glu Asp Arg Glu Thr Leu
                85                  90                  95

Gly Leu Lys Thr Ser Ser Ser Leu Pro Glu Ala Trp Gly Leu Leu Asp
            100                 105                 110

Asp Asp Asp Gly Met Tyr Gly Glu Arg Glu Ala Thr Ser Val Pro Arg
        115                 120                 125

Gly Gln Gly Ser Gln Phe Ala Asp Gly Gln Arg Ala Pro Leu Ser Pro
    130                 135                 140

Ser Leu Leu Ile Arg Thr Leu Gln Gly Ser Asp Lys Asn Pro Gly Glu
145                 150                 155                 160

Glu Lys Ala Glu Glu Glu Gly Val Ala Glu Glu Gly Val Asn Lys
                165                 170                 175

Phe Ser Tyr Pro Pro Ser His Arg Glu Cys Cys Pro Ala Val Glu Glu
            180                 185                 190

Glu Asp Asp Glu Glu Ala Val Lys Lys Glu Ala His Arg Thr Ser Thr
        195                 200                 205

Ser Ala Leu Ser Pro Gly Ser Lys Pro Ser Thr Trp Val Ser Cys Pro
    210                 215                 220

Gly Glu Glu Glu Asn Gln Ala Thr Glu Asp Lys Arg Thr Glu Arg Ser
225                 230                 235                 240

Lys Gly Ala Arg Lys Thr Ser Val Ser Pro Arg Ser Ser Gly Ser Asp
                245                 250                 255
```

-continued

Pro Arg Ser Trp Glu Tyr Arg Ser Gly Glu Ala Ser Glu Lys Glu
            260                 265                 270

Glu Lys Ala His Lys Glu Thr Gly Lys Gly Glu Ala Ala Pro Gly Pro
            275                 280                 285

Gln Ser Ser Ala Pro Ala Gln Arg Pro Gln Leu Lys Ser Trp Trp Cys
        290                 295                 300

Gln Pro Ser Asp Glu Glu Gly Glu Val Lys Ala Leu Gly Ala Ala
305                 310                 315                 320

Glu Lys Asp Gly Glu Ala Glu Cys Pro Pro Cys Ile Pro Pro Ser
            325                 330                 335

Ala Phe Leu Lys Ala Trp Val Tyr Trp Pro Gly Glu Asp Thr Glu Glu
            340                 345                 350

Glu Glu Asp Glu Glu Glu Asp Asp Ser Asp Ser Gly Ser Asp Glu
            355                 360                 365

Glu Glu Gly Glu Ala Glu Ala Ser Ser Ser Thr Pro Ala Thr Gly Val
            370                 375                 380

Phe Leu Lys Ser Trp Val Tyr Gln Pro Gly Glu Asp Thr Glu Glu Glu
385                 390                 395                 400

Glu Asp Glu Asp Ser Asp Thr Gly Ser Ala Glu Asp Glu Arg Glu Ala
                405                 410                 415

Glu Thr Ser Ala Ser Thr Pro Pro Ala Ser Ala Phe Leu Lys Ala Trp
            420                 425                 430

Val Tyr Arg Pro Gly Glu Asp Thr Glu Glu Glu Glu Asp Glu Asp Val
            435                 440                 445

Asp Ser Glu Asp Lys Glu Asp Asp Ser Glu Ala Ala Leu Gly Glu Ala
        450                 455                 460

Glu Ser Asp Pro His Pro Ser His Pro Asp Gln Arg Ala His Phe Arg
465                 470                 475                 480

Gly Trp Gly Tyr Arg Pro Gly Lys Glu Thr Glu Glu Glu Glu Ala Ala
            485                 490                 495

Glu Asp Trp Gly Glu Ala Glu Pro Cys Pro Phe Arg Val Ala Ile Tyr
            500                 505                 510

Val Pro Gly Glu Lys Pro Pro Pro Trp Ala Pro Pro Arg Leu Pro
        515                 520                 525

Leu Arg Leu Gln Arg Arg Leu Lys Arg Pro Glu Thr Pro Thr His Asp
            530                 535                 540

Pro Asp Pro Glu Thr Pro Leu Lys Ala Arg Lys Val Arg Phe Ser Glu
545                 550                 555                 560

Lys Val Thr Val His Phe Leu Ala Val Trp Ala Gly Pro Ala Gln Ala
                565                 570                 575

Ala Arg Gln Gly Pro Trp Glu Gln Leu Ala Arg Asp Arg Ser Arg Phe
            580                 585                 590

Ala Arg Arg Ile Thr Gln Ala Gln Glu Glu Leu Ser Pro Cys Leu Thr
            595                 600                 605

Pro Ala Ala Arg Ala Arg Ala Trp Ala Arg Leu Arg Asn Pro Pro Leu
            610                 615                 620

Ala Pro Ile Pro Ala Leu Thr Gln Thr Leu Pro Ser Ser Val Pro
625                 630                 635                 640

Ser Ser Pro Val Gln Thr Thr Pro Leu Ser Gln Ala Val Ala Thr Pro
            645                 650                 655

Ser Arg Ser Ser Ala Ala Ala Ala Ala Leu Asp Leu Ser Gly Arg
            660                 665                 670

Arg Gly

<210> SEQ ID NO 3
<211> LENGTH: 2225
<212> TYPE: DNA
<213> ORGANISM: Rattus
<220> FEATURE:
<221> NAME/KEY: misc_feature
<222> LOCATION: (0)...(0)
<223> OTHER INFORMATION: rat PEG-3 nucleic acid sequence

<400> SEQUENCE: 3

| | | | | | |
|---|---|---|---|---|---|
| ctgcagtact | tgtacattgc | taaataaaga | gagggactcc | aggaggagca | gcctgggtct | 60 |
| aagaggtagg | cagaaggagg | ttttaggggc | ctgagcacaa | gcttgaggag | agaaaggtta | 120 |
| ttaaaaagcc | agacgcttac | aggtctcaga | agggctagcc | agaaactgtg | gctgggggtta | 180 |
| aggaaagggt | ttaagagtgt | gggcttttgg | ttctgaggat | gtagaacgtg | aatgttgaga | 240 |
| gaagaaccaa | gtggcggagt | tgggtgtgag | caatgctatt | aggaatttga | ggcagggatt | 300 |
| cacgcgctgc | tgtgactatt | ttttaacaat | gactcagtgc | tgtgacctga | tactgtttcc | 360 |
| agagcgactt | ctaaacaaat | tccccctttc | taggccagac | acatggcccc | aagcccaaga | 420 |
| ccccagcatg | tcctgcactg | gaaggaagcc | cactctttct | acctcctgtc | tccactgatg | 480 |
| ggcttcctca | gccgggcctg | gagccgcctg | aggggggcccg | aggtctcaga | ggcctggttg | 540 |
| gcagaaacag | tagcaggagc | aaaccagata | gaggctgatg | ctctgttgac | gcctcccccg | 600 |
| gtctctgaaa | atcacctacc | tctccgagag | actgaaggaa | atggaactcc | tgaatggagt | 660 |
| aaagcagccc | agaggctctg | ccttgatgtg | gaagcccaaa | gttcccctcc | taaaacttgg | 720 |
| ggactttcag | atattgatga | acataatggg | aagccaggac | aagatggcct | tagagagcaa | 780 |
| gaagtggagc | acacagctgg | cctgcctaca | ctacagcccc | ttcacctgca | aggggcagat | 840 |
| aagaaagttg | gggaggtggt | ggctagaaa | gagggtgtgt | ccgagctggc | ttaccccaca | 900 |
| tcacactggg | agggtggtcc | agctgaggat | gaagaggata | cagaaaccgt | gaagaaggct | 960 |
| caccaggcct | ctgctgcttc | catagctcca | ggatataaac | ccagcacttc | tgtgtattgc | 1020 |
| ccaggggagg | cagaacatcg | agccacggag | gaaaaggaa | cagacaataa | ggctgaaccc | 1080 |
| tcaggctccc | actccagagt | ctgggagtac | cacactagag | agaggcctaa | gcaggaggga | 1140 |
| gaaactaagc | cagagcaaca | cagggcaggg | cagagtcacc | cttgtcagaa | tgcagaggct | 1200 |
| gaggaaggag | gacctgagac | ttctgtctgt | tctggcagtg | ccttcctgaa | ggcctgggtg | 1260 |
| tatcgcccag | gagaggacac | agaggaggaa | gaagacagtg | atttggattc | agctgaggaa | 1320 |
| gacacagctc | atacctgtac | cacccccat | acaagtgcct | tcctgaaggc | ctgggtctat | 1380 |
| cgcccaggag | aggacacaga | agaggaagat | gacggtgatt | gggattcagc | tgaggaagac | 1440 |
| gcgtctcaga | gctgtaccac | ccccatacaa | agtgccttcc | tgaaggcctg | ggtctatcgc | 1500 |
| ccaggagagg | acacagaaga | ggaagacgac | agtgagaatg | tggccccagt | tgactcagaa | 1560 |
| acagttgact | cttgccagag | tacccagcat | tgtctaccag | tagagaagac | caagggatgt | 1620 |
| ggagaagcag | agccccctcc | cttccagtgg | ccttctattt | acctggacag | aagccagcac | 1680 |
| caccttgggc | tgcccctaag | ctgccccttc | gactgcagaa | gcggctcaga | tctttcaaag | 1740 |
| cccccgcccg | gaatcagggc | cctgagattc | tctgaaggg | tagaaaggtg | cacttctctg | 1800 |
| agaaagttac | agtccatttc | cttgctgtct | gggcaggacc | agcccaggct | gctcgtcgag | 1860 |
| gcccctggga | gcagtttgca | cgagatcgaa | gccgcttttgc | tcgacgcatt | gccaggcaga | 1920 |
| ggagcagctg | ggtccttacc | ttaccccctgc | tttcagggcc | agagcatgga | cacgccttag | 1980 |

-continued

| | |
|---|---|
| aaacctaccc cttcctctgt cgtcctcgtc tcttccactg cctgagcctt gctcttccac | 2040 |
| tgaggccaca cccctcagcc aagatgtgac cactccctct cccccttccca gtgaaatccc | 2100 |
| tcctcccagc ctggacttgg gaggaaggcg ggctaagcct gagtagtttt ttgtgtattc | 2160 |
| tatgagtgtt agtctcttaa tacgaatatg taacgccttt tgcatttgta aaaaaaaaaa | 2220 |
| aaaaa | 2225 |

<210> SEQ ID NO 4
<211> LENGTH: 2331
<212> TYPE: DNA
<213> ORGANISM: Homo sapien
<220> FEATURE:
<221> NAME/KEY: misc_feature
<222> LOCATION: (0)...(0)
<223> OTHER INFORMATION: GADD34 nucleic acid sequence

<400> SEQUENCE: 4

| | |
|---|---|
| cccagttgtt gatcttatgc aagacgctgc acgaccccgc gcccgcttgt cgccacggca | 60 |
| cttgaggcag ccggagatac tctgagttac tcggagcccg acgcctgagg gtgagatgaa | 120 |
| cgcgctggcc tccctaaccg tccggacctg tgatcgcttc tggcagaccg aaccggcgct | 180 |
| cctgccccg gggtgacgcg cagctcccag ccgcccagac acatggcccc aggccaagca | 240 |
| ccccatcagg ctaccccgtg gagggatgcc caccctttct tcctcctgtc cccagtgatg | 300 |
| ggcctcctca gccgcgcctg gagccgcctg aggggcctgg gacctctaga gccctggctg | 360 |
| gtggaagcag taaaaggagc agctctggta gaagctggcc tggagggaga agctaggact | 420 |
| cctctggcaa tcccccatac cccttggggc agacgccctg aagaggaggc tgaagacagt | 480 |
| ggaggccctg gagaggacag agaaacactg gggctgaaaa ccagcagttc ccttcctgaa | 540 |
| gcctggggac ttttggatga tgatgatggc atgtatggtg agcgagaggc aaccagtgtc | 600 |
| cctagagggc agggaagtca atttgcagat ggccagcgtg ctcccctgtc tcccagcctt | 660 |
| ctgataagga cactgcaagg ttctgataag aacccagggg aggagaaagc cgaggaagag | 720 |
| ggagttgctg aagaggaggg agttaacaag ttctcttatc caccatcaca ccgggagtgt | 780 |
| tgtccagccg tggaggagga ggacgatgaa gaagctgtaa agaaagaagc tcacagaacc | 840 |
| tctacttctg ccttgtctcc aggatccaag cccagcactt gggtgtcttg cccaggggag | 900 |
| gaagagaatc aagccacgga ggataaaaga acagaaagaa gtaaaggagc caggaagacc | 960 |
| tccgtgtccc cccgatcttc aggctccgac cccaggtcct gggagtatcg ttcaggagag | 1020 |
| gcgtccgagg agaaggagga aaaggcacac aaagaaactg ggaaaggaga agctgcccca | 1080 |
| gggccgcaat cctcagcccc agcccagagg ccccagctca gtcctggtg gtgccaaccc | 1140 |
| agtgatgaag aggagggtga ggtcaaggct ttgggggcag ctgagaagga tggagaagct | 1200 |
| gagtgtcctc cctgcatccc cccaccaagt gccttcctga aggcctgggt gtattggcca | 1260 |
| ggagaggaca cagaggaaga ggaagatgag gaagaagatg aggacagtga ctctggatca | 1320 |
| gatgaggaag agggagaagc tgaggcttcc tcttccactc ctgctacagg tgtcttcttg | 1380 |
| aagtcctggg tctatcagcc aggagaggac acagaggagg aggaagatga ggacagtgat | 1440 |
| acaggatcag ccgaggatga aagagaagct gagacttctg cttccacacc ccctgcaagt | 1500 |
| gctttcttga aggcctgggt gtatcggcca ggagaggaca cggaggagga ggaagatgag | 1560 |
| gatgtggata gtgaggataa ggaagatgat tcagaagcag ccttgggaga agctgagtca | 1620 |
| gacccacatc cctcccaccc ggaccagagg gcccacttca ggggctgggg atatcgacct | 1680 |

```
ggaaaagaga cagaggaaga ggaagctgct gaggactggg gagaagctga gccctgcccc    1740
ttccgagtgg ccatctatgt acctggagag aagccaccgc ctccctgggc tcctcctagg    1800
ctgcccctcc gactgcaaag gcggctcaag cgcccagaaa ccctactca tgatccggac      1860 cctgagactc cctaaaggc cagaaaggtg cgcttctccg agaaggtcac tgtccatttc     1920
ctggctgtct gggcagggcc ggccaggc gcccgccagg gccctggga gcagcttgct     1980 cgggatcgca gccgcttcgc acgccgcatc acccaggccc aggaggagct gagcccctgc    2040 ctcaccctg ctgcccgggc cagagcctgg gcacgcctca ggaacccacc tttagccccc    2100
atccctgccc tcacccagac cttgccttcc tcctctgtcc cttcgtcccc agtccagacc    2160
acgcccttga ccaagctgt ggccacacct tcccgctcgt ctgctgctgc agcggctgcc    2220
ctggacctca gtgggaggcg tggctgagac caactggttt gcctataatt tattaactat    2280
ttattttttc taagtgtggg tttatataag gaataaagcc ttttgatttg t            2331
```

<210> SEQ ID NO 5
<211> LENGTH: 605
<212> TYPE: PRT
<213> ORGANISM: Artificial Sequence
<220> FEATURE:
<223> OTHER INFORMATION: rat/human chimera (artificial) amino acid
    sequence of rPEG-3 1-347 + hGADD34 422-674

<400> SEQUENCE: 5

```
Met Ala Pro Ser Pro Arg Pro Gln His Val Leu His Trp Lys Glu Ala
1               5                   10                  15

His Ser Phe Tyr Leu Leu Ser Pro Leu Met Gly Phe Leu Ser Arg Ala
            20                  25                  30

Trp Ser Arg Leu Arg Gly Pro Glu Val Ser Glu Ala Trp Leu Ala Glu
        35                  40                  45

Thr Val Ala Gly Ala Asn Gln Ile Glu Ala Asp Ala Leu Leu Thr Pro
    50                  55                  60

Pro Pro Val Ser Glu Asn His Leu Pro Leu Arg Glu Thr Glu Gly Asn
65                  70                  75                  80

Gly Thr Pro Glu Trp Ser Lys Ala Ala Gln Arg Leu Cys Leu Asp Val
                85                  90                  95

Glu Ala Gln Ser Ser Pro Pro Lys Thr Trp Gly Leu Ser Asp Ile Asp
            100                 105                 110

Glu His Asn Gly Lys Pro Gly Gln Asp Gly Leu Arg Glu Gln Glu Val
        115                 120                 125

Glu His Thr Ala Gly Leu Pro Thr Leu Gln Pro Leu His Leu Gln Gly
    130                 135                 140

Ala Asp Lys Lys Val Gly Glu Val Val Ala Arg Glu Glu Gly Val Ser
145                 150                 155                 160

Glu Leu Ala Tyr Pro Thr Ser His Trp Glu Gly Gly Pro Ala Glu Asp
                165                 170                 175

Glu Glu Asp Thr Glu Thr Val Lys Lys Ala His Gln Ala Ser Ala Ala
            180                 185                 190

Ser Ile Ala Pro Gly Tyr Lys Pro Ser Thr Ser Val Tyr Cys Pro Gly
        195                 200                 205

Glu Ala Glu His Arg Ala Thr Glu Glu Lys Gly Thr Asp Asn Lys Ala
    210                 215                 220

Glu Pro Ser Gly Ser His Ser Arg Val Trp Gly Tyr His Thr Arg Glu
225                 230                 235                 240

Arg Pro Lys Gln Glu Gly Glu Thr Lys Pro Glu Gln His Arg Ala Gly
```

Gln Ser His Pro Cys Gln Asn Ala Glu Ala Glu Gly Gly Pro Glu
             245                 250                 255
                 260                 265                 270

Thr Ser Val Cys Ser Gly Ser Ala Phe Leu Lys Ala Trp Val Tyr Arg
                 275                 280                 285

Pro Gly Glu Asp Thr Glu Glu Glu Asp Ser Asp Leu Asp Ser Ala
                 290                 295                 300

Glu Glu Asp Thr Ala His Thr Cys Thr Thr Pro His Thr Ser Ala Phe
305                 310                 315                 320

Leu Lys Ala Trp Val Tyr Arg Pro Gly Glu Asp Thr Glu Glu Glu Asp
                 325                 330                 335

Asp Gly Asp Trp Asp Ser Ala Glu Glu Asp Ala Leu Thr Ser Ala Ser
                 340                 345                 350

Thr Pro Pro Ala Ser Ala Phe Leu Lys Ala Trp Val Tyr Arg Pro Gly
                 355                 360                 365

Glu Asp Thr Glu Glu Glu Asp Glu Asp Val Asp Ser Glu Asp Lys
                 370                 375                 380

Glu Asp Asp Ser Glu Ala Ala Leu Gly Glu Ala Glu Ser Asp Pro His
385                 390                 395                 400

Pro Ser His Pro Asp Gln Arg Ala His Phe Arg Gly Trp Gly Tyr Arg
                 405                 410                 415

Pro Gly Lys Glu Thr Glu Glu Glu Ala Ala Glu Asp Trp Gly Glu
                 420                 425                 430

Ala Glu Pro Cys Pro Phe Arg Val Ala Ile Tyr Val Pro Gly Glu Lys
                 435                 440                 445

Pro Pro Pro Pro Trp Ala Pro Pro Arg Leu Pro Leu Arg Leu Gln Arg
450                 455                 460

Arg Leu Lys Arg Pro Glu Thr Pro Thr His Asp Pro Asp Pro Glu Thr
465                 470                 475                 480

Pro Leu Lys Ala Arg Lys Val Arg Phe Ser Glu Lys Val Thr Val His
                 485                 490                 495

Phe Leu Ala Val Trp Ala Gly Pro Ala Gln Ala Ala Arg Gln Gly Pro
                 500                 505                 510

Trp Glu Gln Leu Ala Arg Asp Arg Ser Arg Phe Ala Arg Arg Ile Thr
                 515                 520                 525

Gln Ala Gln Glu Glu Leu Ser Pro Cys Leu Thr Pro Ala Ala Arg Ala
                 530                 535                 540

Arg Ala Trp Ala Arg Leu Arg Asn Pro Pro Leu Ala Pro Ile Pro Ala
545                 550                 555                 560

Leu Thr Gln Thr Leu Pro Ser Ser Ser Val Pro Ser Pro Val Gln
                 565                 570                 575

Thr Thr Pro Leu Ser Gln Ala Val Ala Thr Pro Ser Arg Ser Ser Ala
                 580                 585                 590

Ala Ala Ala Ala Ala Leu Asp Leu Ser Gly Arg Arg Gly
                 595                 600                 605

<210> SEQ ID NO 6
<211> LENGTH: 1818
<212> TYPE: DNA
<213> ORGANISM: Artificial Sequence
<220> FEATURE:
<223> OTHER INFORMATION: nucleic acid sequence of rPEG-3 1-347 + hGADD34
      422-674

<400> SEQUENCE: 6

-continued

```
atggccccaa gcccaagacc ccagcatgtc ctgcactgga aggaagccca ctctttctac      60
ctcctgtctc cactgatggg cttcctcagc cgggcctgga gccgcctgag ggggcccgag     120
gtctcagagg cctggttggc agaaacagta gcaggagcaa accagataga ggctgatgct     180
ctgttgacgc ctcccccggt ctctgaaaat cacctacctc tccgagagac tgaaggaaat     240
ggaactcctg aatggagtaa agcagcccag aggctctgcc ttgatgtgga agcccaaagt     300
tcccctccta aaacttgggg actttcagat attgatgaac ataatgggaa gccaggacaa     360
gatggcctta gagagcaaga gtggagcac acagctggcc tgcctacact acagcccctt      420
cacctgcaag gggcagataa gaaagttggg gaggtggtgg ctagaagaa gggtgtgtcc       480
gagctggctt accccacatc acactgggag gtggtccag ctgaggatga agaggataca       540
gaaaccgtga agaaggctca ccaggcctct gctgcttcca tagctccagg atataaaccc     600
agcacttctg tgtattgccc aggggaggca gaacatcgag ccacggagga aaaggaaca      660
gacaataagg ctgaaccctc aggctcccac tccagagtct gggagtacca cactagagag     720
aggcctaagc aggagggaga aactaagcca gagcaacaca gggcagggca gagtcaccct     780
tgtcagaatg cagaggctga ggaaggagga cctgagactt ctgtctgttc tggcagtgcc     840
ttcctgaagg cctgggtgta tcgcccagga gaggacacag aggaggaaga agacagtgat     900
ttggattcag ctgaggaaga cacagctcat acctgtacca cccccatac aagtgccttc      960
ctgaaggcct gggtctatcg cccaggagag acacagaag aggaagatga cggtgattgg     1020
gattcagctg aggaagacgc gttgacttct gcttccacac ccctgcaag tgctttcttg     1080
aaggcctggg tgtatcggcc aggagaggac acggaggag gaagatga ggatgtggat      1140
agtgaggata aggaagatga ttcagaagca gccttgggag aagctgagtc agacccacat    1200
ccctcccacc cggaccagag ggcccacttc aggggctggg gatatcgacc tggaaaagag    1260
acagaggaag aggaagctgc tgaggactgg ggagaagctg agccctgccc cttccgagtg    1320
gccatctatg tacctggaga gaagccaccg cctccctggg ctcctcctag gctgcccctc    1380
cgactgcaaa ggcggctcaa gcgcccagaa acccctactc atgatccgga ccctgagact    1440
cccctaaagg ccagaaaggt gcgcttctcc gagaaggtca ctgtccattt cctggctgtc    1500
tgggcagggc cggccaggc cgcccgccag ggccctggg agcagcttgc tcgggatcgc       1560
agccgcttcg cacgccgcat cacccaggcc caggaggagc tgagccctg cctcacccct      1620
gctgcccggg ccagagcctg gcacgcctg aggaacccac ctttagcccc catccctgcc      1680
ctcacccaga ccttgccttc ctcctctgtc ccttcgtccc cagtccagac cacgcccttg    1740
agccaagctg tggccacacc ttcccgctcg tctgctgctg cagcggctgc cctggacctc    1800
agtgggaggc gtggctga                                                  1818
```

<210> SEQ ID NO 7
<211> LENGTH: 18
<212> TYPE: DNA
<213> ORGANISM: Artificial Sequence
<220> FEATURE:
<223> OTHER INFORMATION: oligonucleotide sense primer

<400> SEQUENCE: 7
atggccccag gccaagca                                                   18

<210> SEQ ID NO 8
<211> LENGTH: 18
<212> TYPE: DNA
<213> ORGANISM: Artificial Sequence -continued

```
<220> FEATURE:
<223> OTHER INFORMATION: oligonucleotide antisense primer

<400> SEQUENCE: 8
aggtcaatat ccccagcc                                              18

<210> SEQ ID NO 9
<211> LENGTH: 18
<212> TYPE: DNA
<213> ORGANISM: Artificial Sequence
<220> FEATURE:
<223> OTHER INFORMATION: oligonucleotide sense primer

<400> SEQUENCE: 9
gacgcgttga cttctgct                                              18

<210> SEQ ID NO 10
<211> LENGTH: 18
<212> TYPE: DNA
<213> ORGANISM: Artificial Sequence
<220> FEATURE:
<223> OTHER INFORMATION: oligonucleotide  antisense primer

<400> SEQUENCE: 10
tcagccacgc ctcccact                                              18

<210> SEQ ID NO 11
<211> LENGTH: 18
<212> TYPE: DNA
<213> ORGANISM: Artificial Sequence
<220> FEATURE:
<223> OTHER INFORMATION: oligonucleotide sense primer

<400> SEQUENCE: 11
tgagacttct gtctgttc                                              18

<210> SEQ ID NO 12
<211> LENGTH: 18
<212> TYPE: DNA
<213> ORGANISM: Artificial Sequence
<220> FEATURE:
<223> OTHER INFORMATION: oligonucleotide antisense primer

<400> SEQUENCE: 12
tggcttctgt ccaggtaa                                              18
```